(12) United States Patent
Tahara et al.

(10) Patent No.: US 9,932,627 B2
(45) Date of Patent: Apr. 3, 2018

(54) METHOD FOR DETERMINATION OF THE LENGTH OF THE G-TAIL SEQUENCE AND KIT FOR THE METHOD

(75) Inventors: Hidetoshi Tahara, Hiroshima (JP); Toshinori Ide, Hiroshima (JP)

(73) Assignee: HIROSHIMA UNIVERSITY, Hiroshima (JP)

( * ) Notice: Subject to any disclaimer, the term of this patent is extended or adjusted under 35 U.S.C. 154(b) by 0 days.

(21) Appl. No.: 13/361,511

(22) Filed: Jan. 30, 2012

(65) Prior Publication Data
US 2012/0190022 A1 Jul. 26, 2012

Related U.S. Application Data

(62) Division of application No. 12/067,710, filed as application No. PCT/JP2006/318783 on Sep. 21, 2006, now abandoned.

(30) Foreign Application Priority Data

Sep. 21, 2005 (JP) .................................. 2005-274523

(51) Int. Cl.
| | |
|---|---|
| *C12Q 1/68* | (2006.01) |
| *C12P 19/34* | (2006.01) |
| *C07H 21/02* | (2006.01) |
| *C07H 21/04* | (2006.01) |

(52) U.S. Cl.
CPC ......... *C12Q 1/6841* (2013.01); *C12Q 1/6827* (2013.01)

(58) Field of Classification Search
CPC ............................ C12Q 1/6827; C12Q 1/6841

USPC ......... 435/6.1, 6.11, 91.1, 183; 436/94, 501; 536/23.1, 24.3, 24.33
See application file for complete search history.

(56) References Cited

U.S. PATENT DOCUMENTS

2003/0199002 A1 10/2003 Hekimi et al.

FOREIGN PATENT DOCUMENTS

| | | |
|---|---|---|
| JP | 02502283 | 7/1990 |
| JP | 2000-350598 | 12/2000 |
| JP | 2001-095586 | 4/2001 |
| WO | WO 98/39485 | 9/1998 |

OTHER PUBLICATIONS

Hausmann et al.,COMBO-FISH: specific labeling of nondenatured chromatin targets by computer-selected DNA oligonucleotide probe combinations. BioTechniques, 35, 564-577, 2003.*
"Exonuclease V". Printed from neb.com on Dec. 5, 2012.*
Chai et al., "Human Telomeres Maintain Their Overhang Length at Senescence", *Molecular and Cellular Biology*, Mar. 2005, p. 2158-2168, American Society for Microbiology.
(Continued)

*Primary Examiner* — Frank Lu
(74) *Attorney, Agent, or Firm* — Richard M. Klein; Fay Sharpe LLP

(57) ABSTRACT

A method of measuring the length of a G tail sequence, characterized by hybridizing the G tail of an nondenatured chromosomal DNA in a sample with a labeled DNA probe having a sequence complementary to the telomere repeat sequence, measuring chemiluminescence from the hybridized DNA probe, and determining the length of the G tail sequence from the measured value, and a kit used for use in such a method.

11 Claims, 23 Drawing Sheets

(56) References Cited

OTHER PUBLICATIONS

Griffith et al., "Mammalian Telomeres End in a Large Duplex Loop", *Cell,* vol. 97, 503-514, May 14, 1999, Cell Press.

Gomez et al., "Interaction of Telomestatin with the Telomeric Single-strand Overhang", *The Journal of Biological Chemistry,* vol. 279, No. 40, Issue of Oct. 1, 2004, pp. 41487-41494, The American Society of Biochemistry and Molecular Biology, Inc.

Tahara et al., "Abnormal telomere dynamics of B-lymphoblastoid cell strains from Werner's syndrome patients transformed by Epstein-Barr virus", *Oncogene* (1997), 15, 1911-1920, Stockton Press.

Van Steensel et al., "TRF2 Protects Human Telomeres from End-to-End Fusions", *Cell,* vol. 92, 401-413, Feb. 6, 1998, Cell Press.

Tahara et al., "G-tail telomere HPA: simple measurement of human single-stranded telomeric overhangs", *Nature Methods,* vol. 2, No. 11, Nov. 2005, 829-831.

Kusunoki et al., "G-tail Telomere HPA: simple measurement of human single-stranded telomeric overhangs", Annual Meeting of the Molecular Biology Society of Japan (Nov. 2005), pp. 518, full text.

Dionne et al., "Cell cycle-regulated generation of single-stranded G-rich DNA in the absence of telomerase", *Proc. Natl. Acad. Sci. USA,* vol. 93, pp. 13902-13907, Nov. 1996, Genetics.

Makarov et al., "Long G Tails at Both Ends of Human Chromosomes Suggest a C Strand Degradation Mechanism for Telomere Shortening", *Cell,* vol. 88, 657-666, Mar. 7, 1997, Cell Press.

Hemann et al., "G-strand overhangs on telomeres in telomerase-deficient mouse cells", *Nucleic Acids Research,* 1999, pp. 3964-3969, vol. 27, No. 20, Oxford University Press.

Karlseder et al., "p53- and ATM-Dependent Apoptosis Induced by Telomeres Lacking TRF2", *Science,* vol. 283, Feb. 26, 1999, pp. 1321-1325.

Nakamura et al., "Simple, Rapid, Quantitative, and Sensitive Detection of Telomere Repeats in Cell Lysate by a Hybridization Protection Assay", *Clinical Chemistry,* 45:10, pp. 1718-1724 (1999), Molecular Diagnostics and Genetics.

Stansel et al., "p53 Binds Telomeric Single Strand Overhangs and t-Loop Junctions in Vitro", *The Journal of Biological Chemistry,* vol. 277, No. 14, Issue of Apr. 5, 2002, pp. 11625-11628, 2002, The American Society for Biochemistry and Molecular Biology, Inc.

Saldanha Sabita, et al. "Assessment of Telomere Length and Factors that Contribute to its Stability", Eur. J. Biochem. V. 270, N. 3, Feb. 1, 2003, pp. 389-403 (2003) © FEBS 2003 Blackwell Publishing, Berlin, Germany XP-008103386.

Cimino-Reale, Graziella, et al. "The Length of Telomeric G-rich Strand 3'-overhang Measured by Oligonucleotide Ligation Assay", Nucleic Acids Research, V. 29, N. 7, Apr. 1, 2001, p. e35, © 2001 Oxford University Press XP-002547121.

Lackey, David B., "A Homogeneous Chemiluminescent Assay for Telomerase", Analytical Biochemistry, V. 263, N. 1, Oct. 1, 1998, pp. 57-61 (1998) XP-002251801.

Nakamura, Yasuhiro, et al., "Simple, Rapid, Quantitative, and Sensitive Detection of Telomere Repeats in Cell Lysate by a Hybridization Protection Assay", Clinical Chemistry V. 45, N. 10, Oct. 1999, pp. 1718-1724 XP-002547122.

\* cited by examiner b Measurement by the measuring method described in Japanese Laid-Open Publication No. 2001-95586

METHOD FOR DETERMINATION OF THE LENGTH OF THE G-TAIL SEQUENCE AND KIT FOR THE METHOD

CROSS-REFERENCE TO RELATED APPLICATIONS

This application is a divisional of U.S. patent application Ser. No. 12/067,710, filed Mar. 21, 2008, now abandoned, which is the National Stage of PCT Application Serial No. PCT/JP2006/318783, filed Sep. 21, 2006, which claimed priority to Japanese Patent Application No. 2005-274523, filed Sep. 21, 2005. These applications are hereby fully incorporated by reference in their entirety.

TECHNICAL FIELD

The present invention relates to a method of measuring the length of a G tail sequence and a kit for use in the method.

BACKGROUND ART

Human chromosomal DNA have double-stranded DNA with repeated sequences of 5'-TTAGGG-3' at the terminus, which are called telomeres. However, the terminal of the telomere has a structure in which the 3"-terminal is an overhang, and a single-stranded DNA region of 75 to 300 bases (G tail, hereinafter referred to simply as G tail). The G tail is normally in a protected state, as a loop is formed, except during the access of a telomere-elongating enzyme telomerase or during the replication of DNA (see, for example, Nonpatent Document 1).

A telomere double-stranded region occupying the most of the telomere is known to be shortened after each cell division and thus involved in cell aging, but the G tail retains a certain length of 75 to 300 bases even after repeated cell division. Contradictorily, there are reports showing that a G tail retains a certain length of 75 to 300 bases after the termination of cell division by the shortening of a telomere double-stranded region after many cell divisions, i.e., after the limited replicative senescence, and some other reports showed that a G tail is shortened after the limited replicative senescence. This is probably because there was no method of measuring the length of a G tail accurately and quantitatively, as the G tail is much shorter than the telomere.

On the other hand, the recent discovery of a POT1 protein binding to a G tail but not to a double-stranded telomere DNA, a PIP1 protein binding to the protein, and the like, has showed that a telomere G tail has a function completely different from that of a double-stranded region, i.e., it is involved in direct signaling of cell death, various cell responses, and the like, as described below.

A telomere has telomere-binding proteins binding to the telomere; TRF1 (Telomere repeat binding factor) and TRF2 are known as such telomere-binding proteins; and it has been recently found that cancer cells do not form a G tail loop in the absence of TRF2 and consequently have shortened G tails (see, for example, Nonpatent Document 2). In such case, what is important is that the G tail is shortened, although the entire telomere length remains unchanged and also fused with the chromosome terminal.

In the case of a normal cell, the elimination of function of TRF2 in the cell leads to the shortening of the G tail, the termination of cell proliferation, and consequently to aging (see, for example, Nonpatent Document 2). In this case too, the entire telomere length remains unchanged, suggesting that the shortening of the G tail triggers aging.

Various proteins such as TRF1 and TRF2 described above, as well as ATM, NBS1, and MRN are known to be essential for the formation of a G tail loop. DNA damage-sensitive signals, e.g., caused for example by various DNA damaging agents or radiation, do not trigger the shortening of the telomere, but induce the shortening of the G tail. This is apparent, since proteins needed for DNA restoration (such as ATM, NBS1 and MRN) are recruited.

ATM is a gene responsible for angiectatic diseases, and NBS1 is a gene responsible for Nijmegen syndromes, i.e., a rare autosomal recessive genetic disease characterized by its high carcinogenicity, immunodeficiency, chromosomal instability, and radiosensitivity. Therefore, the recruitment of these genes to the G tail suggests some relationship of the G tail with the above-described diseases. Actually, the inhibition of the function of TRF2 as the adhesive of a G tail loop induces ATM-dependent apoptosis (see, for example, Nonpatent Document 3).

It has been found that the anticancer agents specifically-acting on a G tail lead to the shortening of the G tail without the shortening of the telomere and consequently to the death of cancer cells (see, for example, Nonpatent Document 4).

These results suggest that medicines and stresses causing DNA damage transmit signals to cells via a G tail, causing various cell responses.

In addition, a cancer-inhibiting gene product p53, of which many variants are observed in many cancers, is known to bind to a G tail (see, for example, Nonpatent Document 5), evidently indicating that the change in the G tail is a signal even in diseases associated with cancers and aging.

Since then, there are developed methods of measuring the length of a G tail, including T-OLA (telomere-oligonucleotide-ligation assay), PENT (primer-extension/nick translation), 3'-overhang protection assay, and the like (see, for example, Nonpatent Documents 6 and 7).

However, as will be described below with reference to Table 1, all these methods demand autoradiography and gel preparation with a radioactive label (such as $^{32}P$), which are troublesome in handling. Also, electrophoresis demands an elongated period for phoretic separation. For these reasons, all these methods are tedious assays demanding at least two days for completion, which are unfavorable for the real-time monitoring of progress of cancer and rapid diagnosis of clinical outcome. In addition, these methods could not be applied easily to the high-throughput screening for analyzing a great number of samples.

Further, in conventional hybridization protection assay (HPA; see, for example, Patent Document 1 and Nonpatent Document 8), which uses a chromosomal DNA after denaturation, the G tail length, which is approximately 1/100 or less of the entire telomere length, is within the range of its operation and measurement errors, and therefore cannot be measured.

Specifically, because the signal intensity of a G tail obtained by the method is so low at the noise level, it is difficult to determine the G tail quantitatively and accurately and also to identify whether the signal is specific to the G tail.

Patent Document 1: Japanese Unexamined Patent Publication No. 2001-95586

Nonpatent Document 1: Griffith J D, Comeau L, Rosenfield S, Stansel R M, Bianchi A, Moss H and de Lange T., Cell: 97 (1999), 503-14.

Nonpatent Document 2: van Steensel B, Smogorzewska A and de Lange T., Cell: 92 (1998), 401-13.

Nonpatent Document 3: Karlseder J, Broccoli D, Dai Y, Hardy S and de Lange T., Science: 283 (1999), 1321-5.

Nonpatent Document 4: Gomez D, Paterski R, Lemarteleur T, Shin-Ya K, Mergny J L and Riou J F. J. Biol. Chem.: 279 (2004), 41487-94.

Nonpatent Document 5: Stansel R M, Subramanian D and Griffith J D., J. Biol. Chem.: 277 (2002), 11625-8.

Nonpatent Document 6: Chai, W., Shay, J. W. & Wright, W. E., Mol. Cell. Biol.: 25, 2158-2168 (2005).

Nonpatent Document 7: Saldanha, S. N., Andrews, L. G. & Tollefsbol, T. O., Eur. J. Biochem.: 270, 389-403 (2003).

Nonpatent Document 8: Nakamura, Y. et al., Clin. Chem.: 45, 1718-1724 (1999).

DISCLOSURE OF THE INVENTION

An objective of the present invention is to provide a method of measuring the length of the sequence of a telomere single-stranded overhang (hereinafter, referred to simply as G tail) specifically and rapidly at high sensitivity without tedious processing operation and denaturation, and a kit for use therein.

After intensive studies to solve the above problems, the inventors of the present invention have found that it is possible to determine the length of a G tail without the denaturation of a chromosomal DNA in a sample, by measuring chemiluminescence intensity through a particular HPA method, especially by measuring the G tail length quantitatively with a calibration curve drawn by using G tail oligomer standards in combination with the amount of chromosomal DNA in the sample and karyotype information on the number of chromosome ends.

The inventors also discovered the fact that the chemiluminescence is specific to the G tail and can be confirmed by a exonuclease treatment. That is, it is possible to determine the length under a condition with a higher ratio in luminescence intensity between the exonuclease treated and untreated samples, i.e., higher in a signal/noise ("S/N") ratio. In addition, a sample concentration condition giving a higher S/N ratio also has been identified. Based on these findings, the inventors have achieved the present invention.

The present invention provides followings:

1. A method of measuring the length of a G tail sequence, comprising hydrizing a G tail of an nondenatured chromosomal DNA in a sample with a labeled DNA probe having a sequence complementary to a telomere repeat sequence, measuring chemiluminescence from the hybridized DNA probe, and determining the length of the G tail sequence from the measured value.

2. The method according to Item 1, wherein the sample is a cell pellet of blood, a cultured cell, a fresh tissue, a cryopreserved tissue or a formalin-fixed tissue.

3. The method according to Item 1 or 2, wherein the fact that the chemiluminescence is based on the hybridization of the labeled DNA probe with the G tail sequence is confirmed by using an exonuclease.

4. The method according to Item 3, wherein the exonuclease is an exonuclease I.

5. The method according to any one of Items 1 to 4, wherein the label is an acridinium ester, luminol, isoluminol, pyrogallol, protohemin, aminobutylethyl-n-isoluminol or aminohexylethyl-n-ethyl-isoluminol.

6. The method according to any one of Items 1 to 5, wherein the sequence complementary to the telomere repeat sequence is a base sequence represented by $(CCCTAA)_n$ (n is an integer of 1 to 10).

7. A kit for measuring the length of a G tail sequence, comprising at least a labeled DNA probe having a sequence complementary to an nondenatured telomere repeat sequence, a cytolytic solution, and a hydrolytic reagent.

8. The kit according to Item 7, further comprising an exonuclease as a confirming agent.

9. The kit according to Item 7 or 8, wherein the label is an acridinium ester, luminol, isoluminol, pyrogallol, protohemin, aminobutylethyl-n-isoluminol or aminohexylethyl-n-ethyl-isoluminol.

10. The kit according to anyone of Items 7 to 9, wherein the sequence complementary to the telomere repeat sequence is a base sequence represented by $(CCCTAA)_n$ (n is an integer of 1 to 10).

11. The method according to any one of Items 1 to 7, wherein the sample is a human- or mouse-derived sample.

The characteristics and advantages of the present invention described above and other advantages will be more apparent to those skilled in the art as described below with reference to attached drawings.

BRIEF DESCRIPTION OF THE DRAWINGS

FIG. 6-1 is a graph showing the change in the amount of chemiluminescence that is dependent on a T7 exonuclease treatment period of an nondenatured DNA.

FIG. 6-2 is a graph in which the rlu value of FIG. 6-1 is converted to an average G tail length by using the calibration curve of FIG. 2.

FIG. 14-1 is a plot showing the linearity in a mouse genomic DNA quantitative determination test by using an internal standard probe A1a.

FIG. 14-2 is a plot showing the linearity in the mouse genomic DNA quantitative determination test by using an internal standard probe A1b.

FIG. 14-3 is a plot showing the linearity in the mouse genomic DNA quantitative determination test by using an internal standard probe A2a.

FIG. 14-4 is a plot showing the linearity in the mouse genomic DNA quantitative determination test by using an internal standard probe A2b.

FIG. 14-5 is a plot showing the linearity in the mouse genomic DNA quantitative determination test by using an internal standard probe B2_1b.

FIG. 14-6 is a plot showing the linearity in the mouse genomic DNA quantitative determination test by using an internal standard probe B2_2a.

FIG. 14-7 is a plot showing the linearity in the mouse genomic DNA quantitative determination test by using an internal standard probe B2_2b.

DESCRIPTION OF THE PREFERRED EMBODIMENTS

Figure 1:
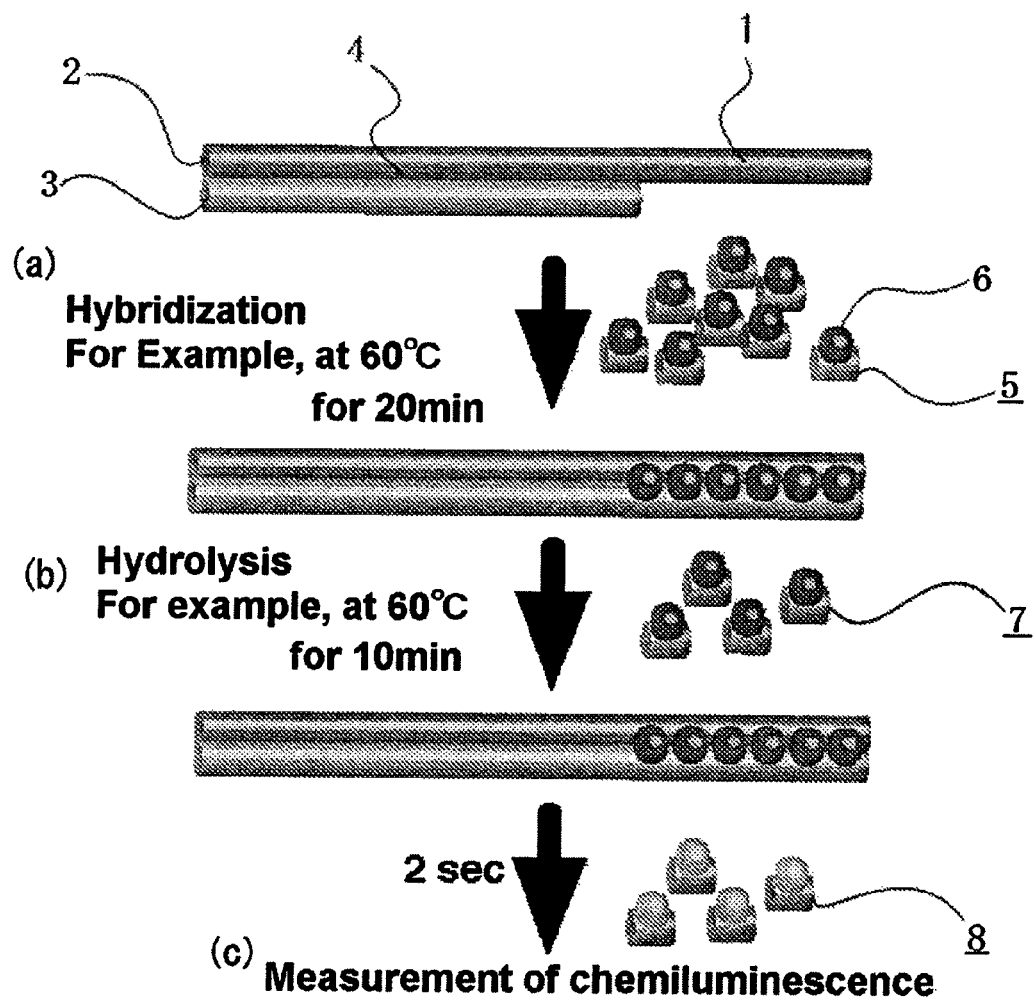
FIG. 1 is a chart showing the summary of a G tail measuring method according to the present invention.

Hereinafter, the present invention will be described in detail.

The method of measuring the length of a G tail sequence according to the present invention is a method of determining the length of the G tail sequence, by hybridizing the G tail with a plurality of labeled probes complementary to the telomere repeat sequence, constituting the G tail by using a hybridization protection assay (HPA) method, and using the amount of chemiluminescence emitted from a nonradioactively labeled substance bound to the probes as an indicator.

In general, the HPA method is a method of using an oligomer labeled with a nonradioactive labeling substance as a probe and detecting luminescence from the nonradioactively labeled substance when the probe is hybridized to a targeted DNA or RNA. The characteristics of the method is that a labeled substance of a free probe is selectively hydrolyzed and the labeling substance is inactivated, instead of a physical separation such as washing performed for the differentiation of a hybridized probe from a unhybridized free probe.

Accordingly, in the present invention, which is based on the HPA method above, a targeted G tail is detected in a short period of time, and the length of the G tail sequence is determined by using the amount of chemiluminescence of the labeled substance as an indicator without a tedious operation such as the amplification of the targeted G tail by PCR and the like.

Hereinafter, the preparation of a cell pellet containing an nondenatured DNA will be described.

In the measuring method according to the present invention, a G tail, which is a single-stranded region in a double-stranded chromosomal DNA, is targeted, and therefore it is possible to use a cell pellet containing an nondenatured chromosomal DNA as a sample.

In the present invention, the cell pellet used as a sample is a pellet of cells recovered after the centrifugation of cells or tissues (e.g., at 1,000 G for 5 minutes).

The pellet may then be washed with a cold phosphate-buffered saline (PBS(−)) twice, frozen rapidly in liquid nitrogen, and stored in a frozen state in liquid nitrogen at low temperature (for example at −80° C.).

During use, for example, it may be resuspended in a hybridization buffer described below, and a suspension solution may be mixed by pipetting and sheared with a 26G syringe before use.

In the present invention, when a cell pellet is used as a sample, the number of cells in the sample is preferably $1 \times 10^5$ to $3.5 \times 10^6$, more preferably $3 \times 10^5$ to $7 \times 10^5$, for the viewpoint of carrying out under a condition higher in the S/N ratio.

When an nondenatured chromosomal DNA is used, the amount of the nondenatured chromosomal DNA used is preferably 0.5 μg to 40 μg, more preferably 1 μg to 20 μg, and particularly preferably 3 μg to 7 μg.

The kind of the cell sample is not particularly limited, if it contains nondenatured chromosomal DNAs, and examples thereof include blood, cultured cells, and various tissues.

The tissue may be arbitrarily selected, independent of the origin of the organ. For example, it may be an tissue in organs such as a cerebral nerve system, muscle and skeleton system, digestive tissues, respiration system, hematopoietic system or lymphatic system. In addition, the tissue may be any tissue, for example, a fresh tissue (immediately after sampling by biopsy), a cryopreserved tissue, or a formalin-fixed tissue.

The measuring method according to the present invention is useful not only for comparison and evaluation of G tail lengths among individuals, but also for comparison and evaluation of the G tail length of the blood or tissue cell among different tissues in a single individual. For example, the G tail lengths of a liver cell, cardiac muscle cell, cerebral nerve cell, and the like, can be compared and evaluated in a single individual.

Further, the tissue is not limited to normal tissues, and tissues with various diseases (such as cancer and hepatic disease) may also be used. For example, cancer-derived tissues include cancer tissues such as of colon cancer and liver cancer; and cancer cell lines such as cell lines of cervical duct cancer, colon cancer, liver cancer, cervical cancer, chronic myelofibrosis, glioblastoma, breast cancer, and fibrosarcoma; and typical examples thereof include SiHa, K562, MKN1, HeLa, U937, U373MG, T98G, A172, MCF-7, HT-1080, LoVo, WiDr, SW857, and VA-4; and the like.

As described above in the measuring method according to the invention, it is not necessary to purify an nondenatured chromosomal DNA from a cultured cell or a human tissue before use, because it is possible to use a cell pellet as it is, but a purified nondenatured chromosomal DNA may be used, as dissolved in a hybridization buffer described below. The nondenatured chromosomal DNA may be purified by any method (see, for example, Tahara H., et al., Oncogene 15 (1997), 1911-1920).

In the present invention, the hybridization buffer which dissolves the sample, the probe described below, and the like, is preferably a buffer which dissolves a cell membrane, a nuclear membrane, and others, because the cell itself may be used as a sample. Examples thereof include a lithium succinate buffer containing a laurylsulfate salt, lithium chloride, EDTA and EGTA, and the like.

Hereinafter, the labeled HPA probe for use in the present invention will be described.

The labeled HPA probe for use in the present invention is an oligonucleotide having a base sequence represented by $(CCCTAA)_n$ (n is an integer of 1 to 10) that is labeled with at least one nonradioactive labeling substance, n is properly selected according to a desired chromosomal DNA, but preferably 2 to 8, more preferably 3 to 5.

The oligonucleotide for use as a probe can be prepared by a commercially available DNA synthesizer by any DNA-producing method such as the phosphoamidite method. During chemical synthesis, an amino linker is preferably introduced for labeling with a nonradioactive labeling substance.

Examples of reagents for the introduction of an amino linker when the phosphamidite method is used include, for example, the following linker-introducing reagents 1 to 3.

[Formula 1]

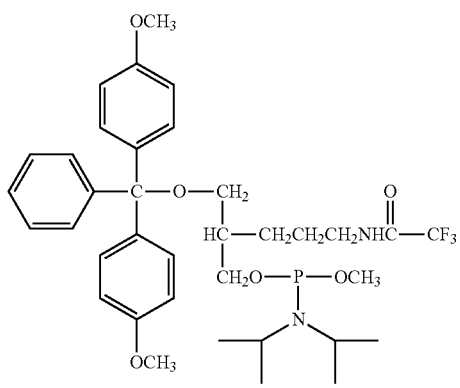

Linker-introducing agent 1

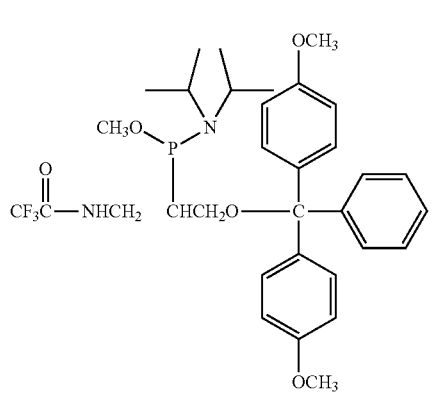

Linker-introducing agent 2

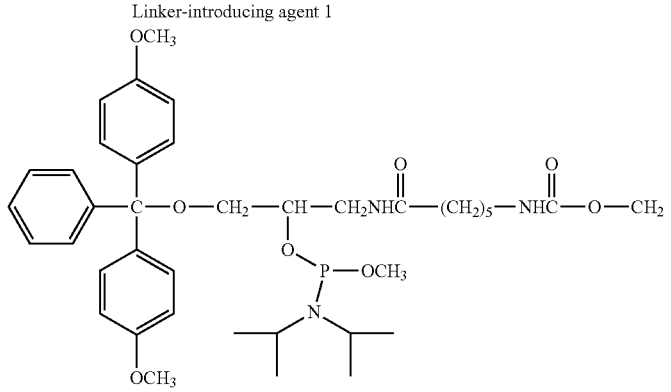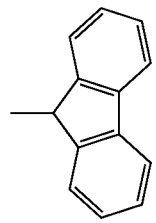

Linker-introducing agent 3

The oligonucleotide containing the introduced amino linker can be prepared, for example, according to the method described in Japanese Patent No. 3483829.

An acridinium ester in the present invention (hereinafter, referred to simply as AE) is the following compound 4-(2-succinimidyloxycarbonylethyl)phenyl 10-methyl acridinium-9-carboxylate having a phenyl ester group.

[Formula 2]

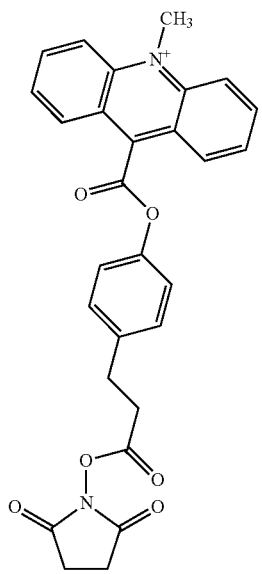

With the compound AE, an oligonucleotide which introduced the amino linker by the reaction of an N-hydroxysuccinimide ester in the AE with an amino group in the amino linker introduced as described above, can be labeled. Thus, a labeled HPA probe for use in the present invention is constructed The labeling method with AE and the operation procedure can be performed, for example, according to the method described in Japanese Patent No. 3483829.

The labeling site, for example with AE, can be determined arbitrarily according to the position of an amino linker introduced during DNA synthesis (Japanese Unexamined Patent Publication No. 2-502283).

Such a labeled HPA probe is available, for example, form Gene Probe Inc., and an example thereof is an AE-labeling G tail HPA probe (5'-CCCTAACCCTAACC*CTAACCCTAACCCTA-3', SEQ ID No. 1, 29 bases). * indicates the AE labeling site, and, as described above, an amino group in an amino linker introduced to a oligonucleotide with the introducing reagent 1, 2 or 3 is labeled by the reaction with an N-hydroxysuccinimide ester in AE.

Examples of the nonradioactive labeling substances include, in addition to the compound AE, luminol, isoluminol, pyrogallol, protohemin, aminobutylethyl-n-isoluminol and aminohexylethyl-n-ethyl-isoluminol. The nonradioactive labeling substance has a substituent forming a chemical bond with the amino group in the amino linker introduced to the oligonucleotide. Examples of such a substituent group include, for example, a N-hydroxysuccinimide ester group.

Examples thereof are not limited to the labeling substances above and include, for example, acridine derivatives represented by the following General Formula (I):

[Formula 3]

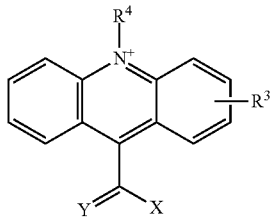

(I)

wherein X represents a halogen atom or a group represented by the following General Formula (II):

[Formula 4]

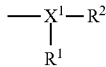

(II)

wherein $X^1$ represents a nitrogen, phosphorus, boron or arsenic atom; $R^1$ represents an alkoxy or aryloxy group or a substituted or unsubstituted alkyl, alkenyl or aryl group; and $R^2$ represents a hydrogen atom, an alkoxy or aryloxy group, or a substituted or unsubstituted alkyl, alkenyl or aryl group, or a group represented by the following General Formula (III):

 (III)

wherein $X^2$ represents an oxygen or sulfur atom; and $R^2$ is the same as that above; Y represents an oxygen or sulfur atom or a NH group; $R^3$ represents a hydrogen atom, an amino, hydroxy, thiol, carboxylic acid, halogen, nitro, alkoxy or aryloxy group, or a substituted or unsubstituted acetyl, alkyl, alkenyl or aryl group; $R^4$ represents a substituted or unsubstituted alkyl, alkenyl or aryl group; and at least one group of $R^1$, $R^2$, $R^3$ and $R^4$ contains a reactive site forming a chemical bond with the amino linker.

Here, examples of the halogen include, for example, a fluorine, chlorine, bromine, iodine or astatine atom. The alkyl groups are those having 1 to 20 carbon atoms, preferably 1 to 5 carbon atoms, such as methyl, ethyl, propyl, butyl, amyl and the like. The alkenyl groups are those having 1 to 10 carbon atoms, preferably having 1 to 5 carbon atoms, such as example vinyl, allyl and the like. The aryl groups are, for example, phenyl, tolyl, naphthyl, xylyl and the like. The alkoxy groups are, for example, those having 1 to 10 carbon atoms, preferably having 1 to 5 carbon atoms, such as methoxy and ethoxy; and the aryloxy groups are, for example, phenoxy, naphthoxy and the like.

The method of measuring the length of a G tail sequence according to the present invention will be described with reference to FIG. 1.

FIG. 1 is a chart showing the summary of the G tail measuring method according to the present invention, in which reference numeral 1 represents a G tail; reference numeral 2 represents a telomere G-strand; reference numeral 3 represents a telomere C-strand; reference numeral 4 represents a double-stranded telomere region, reference numeral 5 represents a labeled (HPA) probe, reference numeral 6 represents the compound AE, reference numeral 7 represents an unhybridized probe; and reference numeral 8 represents a probe inactivated by hydrolysis. The G tail 1 is located at the terminal of the G-strand of the telomere double-stranded region 4 consisting of chromosomal DNA terminal of the telomere G-strand 2 and C-strand 3.

The AE-labeled probe 5 for use in the present invention is labeled with the AE 6 and has a sequence complementary to a repeat sequence in the G tail, and the probes in the number corresponding to the repetition number of the repeat sequences are bound thereto by hybridization, as shown in FIG. 1(a).

The hybridization between the AE-labeled probe 5 and the G tail 1 is specifically performed by adding a hybridization solution containing the AE 6-labeled probe to a cell pellet and then incubating the mixture, for example, at 60 to 65° C. for 5 to 30 minutes (heated incubation).

The AE-labeled probe 5 hybridized with the G tail 1 has the AE stabilized; the ester bond of the AE remains protected even after hydrolysis for a certain period in FIG. 1(b); the addition of an alkali and hydrogen peroxide leads to chemiluminescence; and thus, it is possible to determine the length of the G tail 1 by measuring the amount of luminescence quantitatively, as shown in FIG. 1(c).

On the other hand, in the probe 7, which remains unhybridized with the G tail 1, the AE is not stabilized. When the hydrolysis of (b) is performed in that state, the ester bond of the AE is hydrolyzed, giving an inactivated probe 8 that shows no chemiluminescence, thus prohibiting the detection of the inactivated probe 8.

For the elimination of chemiluminescence due to unreacted probe, specifically during the hydrolysis (b), a hydrolysis reagent is added, and the mixture is incubated at 60° C. for 5 to 10 minutes. The measurement of chemiluminescence of the AE in FIG. 1(c) after incubation is carried out by using a luminometer (for example, Leader I (trade name, manufactured by Gene Probe Inc.)). In particular, the use of a 96-well luminometer is preferable for high-throughput screening by using the measuring method according to the invention.

In the measuring method according to the invention, it is preferable to confirm that the chemiluminescence is G tail-specific by eliminating a G tail sequence selectively by treating a DNA sample with an exonuclease I (ExoI) in such a manner that exonuclease removes a single-stranded nucleotide in the 3' to 5' direction.

In addition, the ratio of the signal of the ExoI-unpretreated sample to that of the ExoI-treated sample may be calculated as an S/N ratio. Thus, it is possible to measure the G tail length specifically, even if there are some contaminants present in the sample.

Further, it is also possible to confirm that the chemiluminescence is G tail sequence-specific, by treating the G tail with T7 exonuclease, removing the telomere C-strand 3 in the 5' to 3' direction, and elongating the G tail on the telomere G-strand 2.

In the method according to the present invention described above, for example, if the G tail has sequences obtained by repeating a base unit sequence (5'-TTAGGG-3') 24 times and the probe is [5'-(CCCTAA)$_4$-3'] in which a (5'-CCCTAA-3') sequence is repeated four time, theoretically, six probes hybridize to the G tail. Accordingly, labels corresponding to six probes is detected. It is possible to calculate the length of the G tail sequence, by previously drawing a calibration curve by determining the label intensity when the probe is hybridized with standard DNA reagents of known lengths.

It is also possible to determine the length of the G tail by measuring the chemiluminescence intensity quantitatively, when an acridine derivative other than AE or another nonradioactive labeling substance (e.g., luminol, isoluminol, pyrogallol, protohemin, aminobutylethyl-n-isoluminol, or aminohexylethyl-n-ethyl-isoluminol) is used as the label. Specifically, a probe labeled with the acridine derivative or another nonradioactive labeling substance is allowed to react with the cell pellet in a suitable amount; after the reaction, the mixture is processed, for example, by hydrolysis; and then, the amount of chemiluminescence is determined quantitatively.

The Alu sequence is a base sequence represented by 5'-GCCTCCCAAAGTGCTGGGATTACA-3' (SEQ ID No. 3), the amount of which in the chromosomal DNA is known to be constant also in cultured cell (J. D. Watson Ed., Molecular Biology of the Gene, p. 668). It is possible to determine the amount of the G tail sequence in a certain amount of the chromosomal DNAs, by measuring the amount of the Alu sequence added as an internal standard to each sample and determining the ratio of the G tail sequence and the Alu sequence during the measurement of the G tail. In this way, it is possible to calculate the average length of the G tail sequence.

TABLE 1

Comparison of the measuring method of the present invention with traditional measuring methods

| Method | Detection range (nt) | Detection period | RI[a] | Direct measurement of cells | Electrophoresis | Distribution of G-tail length | High throughput |
| --- | --- | --- | --- | --- | --- | --- | --- |
| T-OLA | 24-650 | 2 days | Necessary | Not possible | Necessary | Possible | Not possible |
| PENT | 130-210 | 2 days | Necessary | Not possible | Necessary | Possible | Not possible |
| electrom microscopy | 225-650 | 2 days | Necessary | Not possible | Necessary | Possible | Not possible |
| 3'-overhang protection assay | 45-384 | 2 days | Necessary | Not possible | Necessary | Not possible | Not possible |
| Measuring method of the present invention | 20-1600< | 40 min. | Unnecessary | Possible | Unnecessary | Not possible | applicable[b] |

[a]RI: Radioisotope,
[b]96-multi-plate screening

Hereinafter, the kit for measuring the length of a G tail sequence according to the present invention will be described.

The kit according to the present invention is a set containing at least a labeled DNA probe having a sequence complementary to an nondenatured telomere repeat sequence (e.g., $(CCCTAA)_n$ (n is an integer of 1 to 10)), a cytolytic solution, and a hydrolytic reagent. Examples of such labeled DNA probes include those described above as labeled HPA probes, and the specific examples and the favorable range thereof are the same as those above.

Examples of the cytolytic solution include, for example, a lithium succinate buffer containing a laurylsulfate salt, lithium chloride, and EDTA and EGTA. Examples of the hydrolytic reagent include, for example, a tetrasodium borate buffer containing Triton X-100.

The kit according to the present invention preferably contains a standard for the formation of a G tail length calibration curve (G tail sequence preferably having 20 bases or more, more preferably 30 to 100 bases).

The kit more preferably contains a standard for the formation of a calibration curve for the normalization of a chromosomal DNA amount (synthetic Alu-sequence DNA preferably having 20 bases or more, more preferably 30 to 100 bases) and an Alu-HPA probe for the normalization of the chromosomal DNA amount (e.g., 5'-TGTAATCCCA*GCACTTTGGGAGGC-3'; *: AE-labeling site, SEQ ID No. 2).

The kit still more preferably contains an exonuclease (e.g., ExoI, T7 exonuclease, or the like, preferably ExoI) as a confirming agent.

The kit may contain additionally, for example, a purified chromosomal DNA of any cancer cell as a positive control DNA.

Hereinafter, the measuring method according to the invention and the traditional method will be compared with reference to Table 1.

As apparent from Table 1, the traditional methods demand a radioactive label (RI) and gel preparation, which are troublesome in handling and require electrophoretic separation which demands an elongated period. Therefore, these methods are tedious assays demanding at least two days for completion, and cells can not be used without processing for measurement. In addition, these traditional methods may be applied to high-throughput screening for analyzing a great number of samples.

On the other hand, the method according to the present invention, which does not used radioactive materials, does not demand any special waste-processing facility or an electrophoretic device or the like for the separation of the reactive products and the unreacted radioactive materials. It is also possible to measure short length G tails of up to 20 nucleotides specifically, quantitatively and at high sensitivity, by using a single container (e.g., test tube), within a short period (about 40 minutes or less) from the collection of the tissues. In addition, it is possible to determine the length of the G tail reproducibly, as the measurement results are less dispersed and to handle a great number of samples easily. Furthermore, the measuring method according to the present invention allows the measurement not only of nondenatured chromosomal DNAs but also of cells directly, and is thus applicable to the high-throughput screening for analyzing a great number of samples.

A genomic DNA may be collected not in an intact (uncleaved) state, and thus, it is possible to determine the G tail length of cultured cells, fresh tissues, and others, as well as tissues stored for a long period (e.g., formalin-fixed tissues). Furthermore, by the method according to the present invention, it is possible to obtain detection results high in sensitivity than those obtained by conventional detection methods. Specifically, the sensitivity with a purified DNA is about 1000 times higher than that of the Southern method, and the method of the present invention allows analysis of several (ng) of a genomic DNA.

Hereinafter, the advantageous effects of the present invention will be described. According to the method of measuring the length of a G tail sequence according to the present invention, it is possible to measure a short-length G tail of up to 20 nucleotides specifically and quantitatively at high sensitivity, only in 3 steps without the denaturation of a telomere or any tedious processing.

In addition, the measuring method according to the present invention allows analysis not only of nondenatured chromosomal DNAs but also of cells directly as samples and thus, acceleration of analysis, and is applicable, for example, to the high-throughput screening for analyzing a great number of samples.

Furthermore, it is possible to analyze a small amount of cells of $5 \times 10^5$ cells or less directly; the chromosomal DNA is not lost during sample preparation; and thus, the method of the present invention is useful in the cases where the number of the cells obtained is limited, for example, during blood test or analysis of clinical samples such as biopsy and urine for cancer cell analysis.

With the kit for measuring the length of a G tail sequence according to the present invention, it is possible to measure the length of the G tail sequence in a sample within 40 minutes by using only a single container (e.g., test tube).

The measuring method according to the present invention can be used clinically for patients with various diseases associated with cancer and aging, which may proceed as a result of G tail loss.

The measuring method according to the invention is useful in basic research on cancer, aging, and the biological impacts caused by telomere abnormality.

EXAMPLES

Hereinafter, the present invention will be described in detail with reference to Examples, but it should be understood that the present invention is not restricted thereby.

Example 1

<1-1> Test for Confirming Dose-Response of Synthetic Single-Stranded G Tail

For the confirmation of dose-response relationship by the measuring method according to the invention, the following hybridization buffer diluents containing a 84-base single-stranded synthetic G tail, 5'-(TTAGGG)$_{14}$-3' (manufactured by Prorigo) at various concentrations and an AE-labeled G tail HPA probe (5'-CCCTAACCCTAACC*CTAACCCTAACCCTA-3, SEQ ID No. 1, *: AE-labeling site, 29 bases) having a amount of chemiluminescence of $3 \times 10^7$ relative light units (hereinafter, referred to simply as rlu) were incubated and allowed to hybridize with each other in 100 μL of the following hybridization buffer at 60° C. for 20 minutes.

The AE-labeled G tail probe was prepared by labeling, with AE, an amino linker-introduced oligonucleotide (SEQ ID No. 1) prepared by using the linker-introducing reagent 3, according to the method described in Japanese Patent No. 3483829.

TABLE 2

Composition of hybridization buffer 0.1 mol/L Lithium succinate buffer, pH 4.7
200 g/L Lithium laurylsulfate
1.2 mol/L Lithium chloride
20 mmol/L EDTA Here, EDTA represents ethylenediaminetetraacetic acid, while EGTA represents ethylene glycol bis(2-aminoethylether)tetraacetic acid.

<1-2> Hydrolysis of Unhybridized Probe and Detection of Chemiluminescence

The hydrolysis of the AE in an unhybridized probe was performed by charging 300 μL of a hydrolysis buffer (0.6 mol/L tetrasodium borate buffer containing 50 mL/L of Triton X-100, pH 8.5) into each reaction tube, stirring the mixture vigorously with a Vortex mixer, and incubating the mixture at 60° C. for 10 minutes. The AE in the hybridized probe was not hydrolyzed under the above-described condition. These tubes were cooled on ice for 1 minute or more, and the chemiluminescence in each tube was measured with a luminometer (trade name: Leader 1, manufactured by Gene Probe Inc.) for 2 seconds.

<1-3> Results

Figure 2:
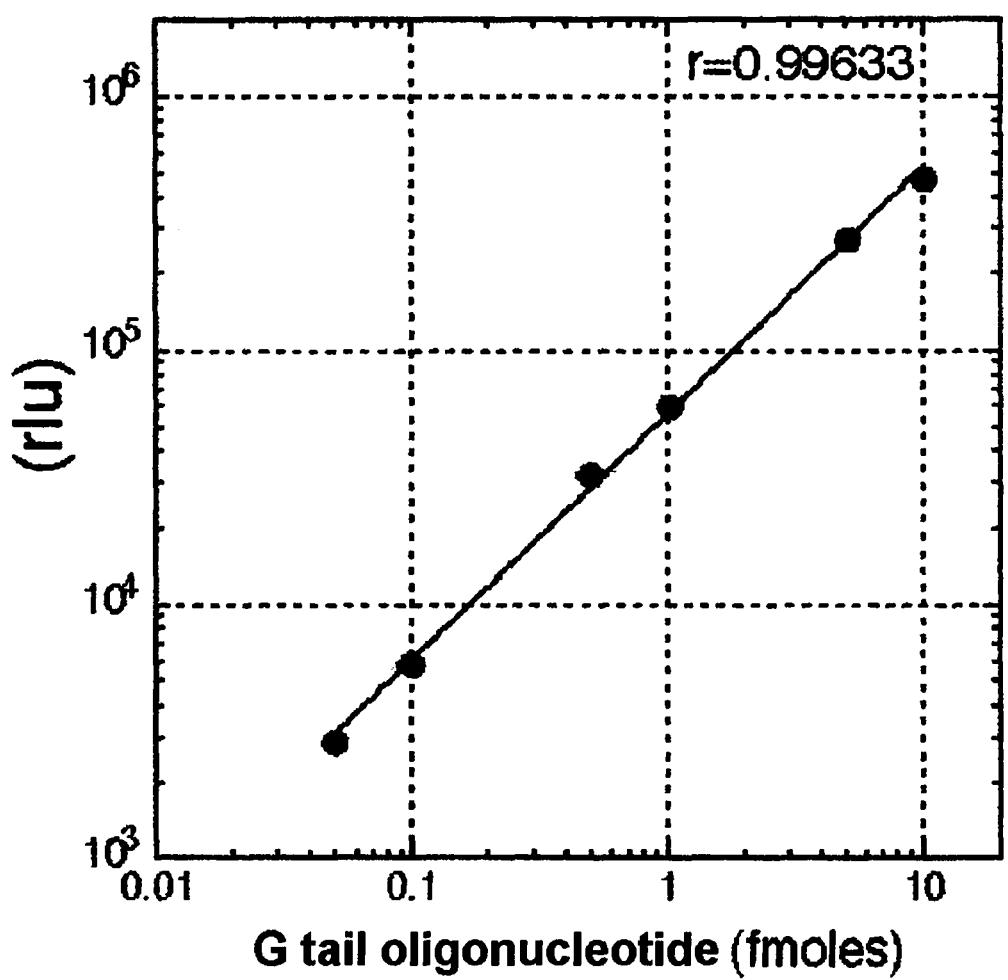
FIG. 2 is a graph showing the results of a dose-response test between a 29-base AE-labeled G tail HPA probe and a 84-base single-stranded synthetic G tail.

FIG. 2 is a graph showing the results of the dose-response test carried out between the 29-base AE-labeled G tail HPA probe and the single-stranded synthetic G tail (84 bases). As apparent from FIG. 2, increase in oligonucleotide dosage in the range of 0.05 fmol to 10 fmol is accompanied by a linear increase of signal intensity.

<2-1> Specificity Confirmation Test

It was to confirm whether the 29-base AE-labeled G tail HPA probe detects the 5'-TTAGGG-3' repeat sequence constituting the G tail specifically. The following various 84-base G tail single-stranded DNAs (10 fmol), which are single base substitution variants of WT (wild type) G tail, were hybridized respectively with the 29-base AE-labeled G tail HPA probe under a condition similar to that in <1-1> above:

WT [5'-(TTAGGG)$_{14}$-3'];
variant G tail oligonucleotide A [5'-(TTGGGG)$_{14}$-3'];
variant G tail oligonucleotide B [5'-(TTAAGG)$_{14}$-3'];
variant G tail oligonucleotide C [5'-(TTCGGG)$_{14}$-3']; and
variant G tail oligonucleotide D [5'-(TTAGGC)$_{14}$-3']
(all G tail DNAs from Prorigo).

The hydrolysis of the AE in the unhybridized probe and the detection of the chemiluminescence were performed under a condition similar to that in <1-2>.

<2-2> Results

Figure 3:
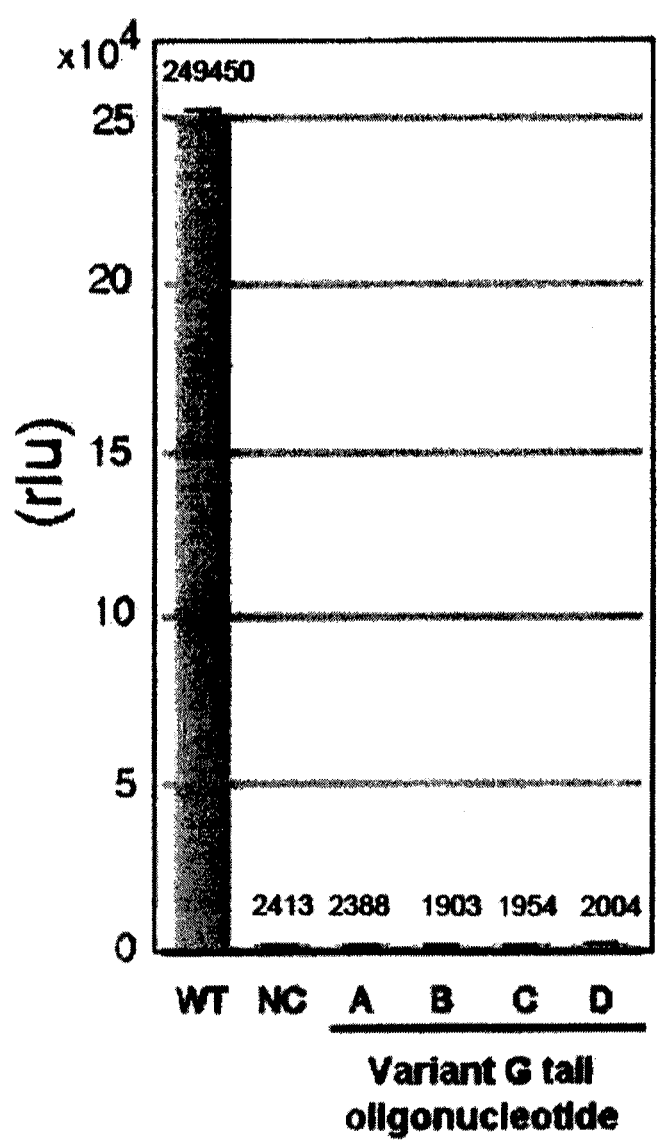
FIG. 3 is a graph showing the results of a specificity confirmation test.

FIG. 3 is a graph showing the results of the specificity confirmation test. In FIG. 3, WT represents a wild-type single-stranded G tail sequence; the variant G tail nucleotide A represents 5'-(TTGGGG)$_{14}$-3; the variant G tail nucleotide B represents 5'-(TTAAGG)$_{14}$-3'; the variant G tail nucleotide C represents 5'-(TTCGGG)$_{14}$-3'; the variant G tail nucleotide D represents 5'-(TTAGGC)$_{14}$-3'; and NC represents a negative control. NC represents the background signal level in the test. As apparent from FIG. 3, the HPA probe for use in the present invention detects the desired mammal G tail sequence specifically at a high S/N ratio.

<3-1> Test for Confirming Alkali Treatment Resistance of AE

A test for confirming an alkali treatment resistance of AE was performed, to know how many complete nucleotide base pairs are needed for the hybridization between the G tail and the AE-labeled G tail HPA probe (29 bases) for the chemiluminescence of the AE. By using a single-strand G tail (WT) having a base length of 29 bases similar to the AE-labeled G tail HPA probe above, the following 29-base variant G tail (Mu) containing a point mutation at a position five bases separated from the probe-labeling site, the common AE-labeled G tail HPA probe, and the following three kinds of variant AE-labeled G tail HPA probes (Mut1, Mut2 and Mut3), the combinations (i), (ii), (iii), (iv) and (v) shown in FIG. 4 were hybridized under a condition similar to that in <1-1>, and the amount of chemiluminescence based on that of the AE was measured. The hydrolysis of the AE in the unhybridized probe and the detection of the chemiluminescence were performed under a condition similar to that in <1-2>.

Mu: 5'-TAGGGTTAGGGTTAGGGTTAGGGTTAGGG-3' (SEQ ID No. 4, variant G tail)

Mut1: 5'-CCCTAAC*CATAACCCTAACCCTAACCCTA-3' (SEQ ID No. 5, *: AE-labeling site, underline: point mutation site, 29 bases)

Mut2: 5'-CCCTAACCA*TAACCCTAACCCTAACCCTA-3' (SEQ ID No. 6, *: AE-labeling site, underline: point mutation site, 29 bases)

Mut3: 5'-CCCTAACCATAACC*CTAACCCTAACCCTA-3' (SEQ ID No. 7, *: AE-labeling site, underline: point mutation site, 29 bases)<

<3-2> Results

Figure 4:
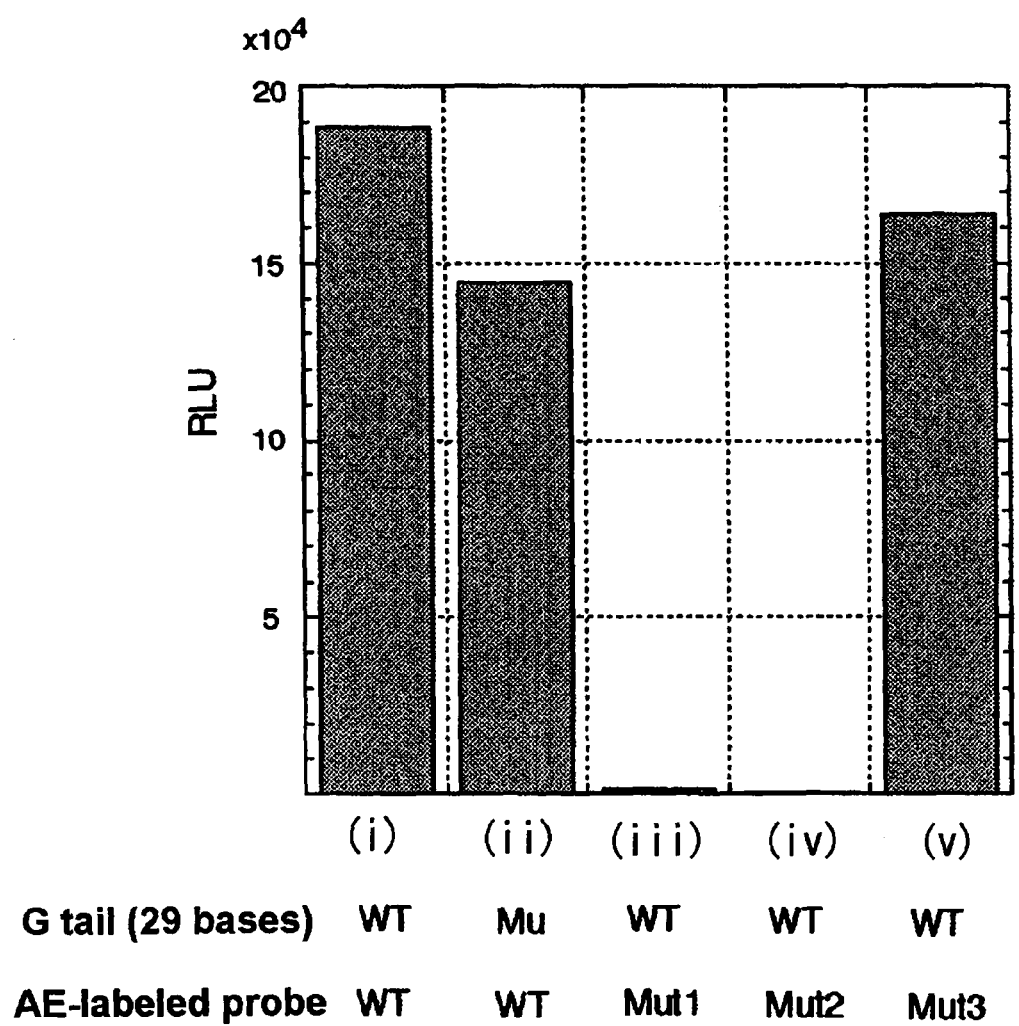
FIG. 4 is a graph showing the amount of an AE-based chemiluminescence in each combination.

FIG. 4 is a graph showing the amount of chemiluminescence in each combination on the basis of that of the AE. As apparent from FIG. 4, there was almost no chemiluminescence detected in combinations mismatched at the AE-labeling site (iv) and mismatched at the position one base separated from the AE-labeling site (iii). In the cases where the position five bases separated from the AE-labeling site is mismatched ((ii) and (v)), there was only slight deterioration in chemiluminescence. The results indicated that mismatching at a position about six bases separated from the AE-labeling site had no influence on HPA chemiluminescence.

<4-1> Test for Confirming Nondenatured Genomic DNA Dose Response and G Tail Specificity (1)

For the confirmation of nondenatured genomic DNA dose response by the measuring method according to the invention, SiHa cancer cell line-derived nondenatured genomic DNA samples in various amounts (1 µg, 3 µg, 5 µg, 10 µg and 20 µg) and the AE-labeled G tail HPA probe in an amount of 3×10$^6$ rlu were hybridized with each other. Specifically for detection of the telomere 3'-tail (G tail) in genomic DNA, the total amount of the DNA solution in a Falcon 352053 tube (trade name) was adjusted to 100 µL with sterile water or a TE buffer (10 mM Tris/HCl, 1 mM EDTA, pH 8.0). The AE-labeled G tail HPA probe in an amount of 3×10$^6$ rlu dissolved in 100-µL of the hybridization buffer was added to the DNA solution, and the mixture was stirred thoroughly with a Vortex mixer and incubated at 60° C. for 20 minutes. The hydrolysis of the AE in unhybridized probe and the detection of the chemiluminescence were performed under a condition similar to that in <1-2>.

<4-2> Isolation of Nondenatured Genomic DNA

In the present invention, the nondenatured genomic DNA may not be isolated for use, but the nondenatured genomic DNA used in the confirmation test <4-1> was previously isolated in the following manner: The nondenatured genomic DNA used for G tail length measurement was isolated from each cell line by using the phenol-chloroform extraction method. Specifically, cells were centrifuged in an Eppendorf-micro centrifuge tube at 6,000 rpm and 4° C. for 5 minutes, to give a pellet in the microtube. The pellet was washed once with PBS(−) and resuspended in an extraction buffer containing 10 mM Tris buffer (pH 7.6), 150 mM NaCl and NP-40, to a final concentration of 0.5%. After proteinase K digestion, phenol-chloroform extraction was performed twice. The genomic DNA was precipitated with ethanol, treated with RNase A, and then, dissolved in a TE buffer.

<4-3> Exonuclease I Treatment for Confirmation of G Tail Specificity

The nondenatured genomic DNA was treated with exonuclease I (ExoI) that removes a single-stranded nucleotide selectively in the 3' to 5' direction, eliminating the G tail sequence selectively, consequently confirming that the chemiluminescence was G tail-specific. The exonuclease I treatment of the nondenatured genomic DNA was performed in the following manner: The genomic DNA was treated with ExoI (manufactured by New England Biolabs, 0.2 U/µg-DNA) in 1× exonuclease buffer (67 mM glycine-KOH (pH 9.5), 6.7 mM MgCl$_2$, 10 mM 2-mercaptoethanol) at 37° C. for 2 hours, and the exonuclease was inactivated under heat at 80° C. for 20 minutes before the G tail assay.

<4-4> Results

Figure 5:
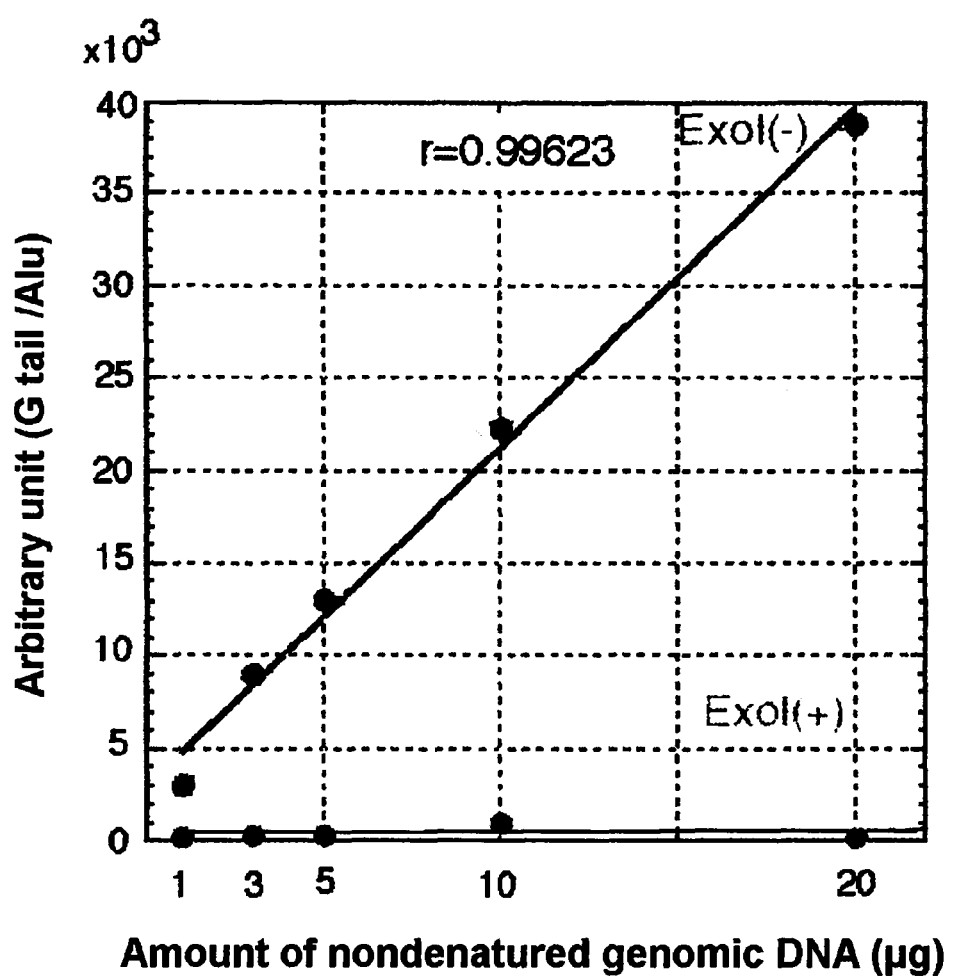
FIG. 5 is a graph showing the results obtained by using a genomic DNA previously treated with ExoI before a G tail assay, and an untreated sample.

FIG. 5 is a graph showing the results obtained by using the genomic DNA previously treated with ExoI before a G tail assay and that not treated therewith. It is a graph obtained by plotting the total genomic DNA amount normalized into arbitrary unit, obtained by denaturing a 1/20 amount of the nondenatured genomic DNA by the method described below and hybridizing it with the AE-labeled Alu probe in an amount of 3×10$^6$ rlu. As apparent from FIG. 5, a linear response was observed at the nondenatured genomic DNA amount in the range of 1 µg to 20 µg. The results indicate that 5 µg of nondenatured genomic DNA may be used normally. FIG. 5 indicates that all sample were ExoI-sensitive and the detected chemiluminescence is specific to the single-stranded G tail, and the comparison between the ExoI-pretreated graph and ExoI-unpretreated graph reveals that an extremely large S/N ratio is obtained in the measurement range.

<5-1> G Tail Specificity Confirmation Test (2) and Measurement of the Length of a G Tail Sequence First, the nondenatured genomic DNA was treated with T7 exonuclease, eliminating the telomere C-strand in the 5' to 3' direction and elongating the G tail in the telomere G-strand, consequently revealing that chemiluminescence was G tail-specific. The SiHa cancer cell line-derived nondenatured genomic DNA (5 µg) was treated with T7 exonuclease in the following manner: The genome DNA was incubated with T7 exonuclease (manufactured by New England Biolabs, 1 U/µg-DNA) in 1×NE Buffer 4 (50 mM potassium acetate, 20 mM Tris acetate, 10 mM magnesium acetate, 1 mM dithiothreitol, pH 7.9) at 25° C. for the period shown in the Figure. The reaction was terminated by addition of EDTA (pH 8.0) to a final concentration of 25 mM.

<5-2>

The incubation and hybridization of the AE-labeled G tail HPA probe and the nondenatured DNA in the hybridization buffer for the detection of the G tail were performed under a condition similar to that in <4-1> above. The hydrolysis of the AE in the unhybridized probe and detection of the chemiluminescence were performed under a condition similar to that in <1-2>.

<5-3> Result

Figures 1, 6:
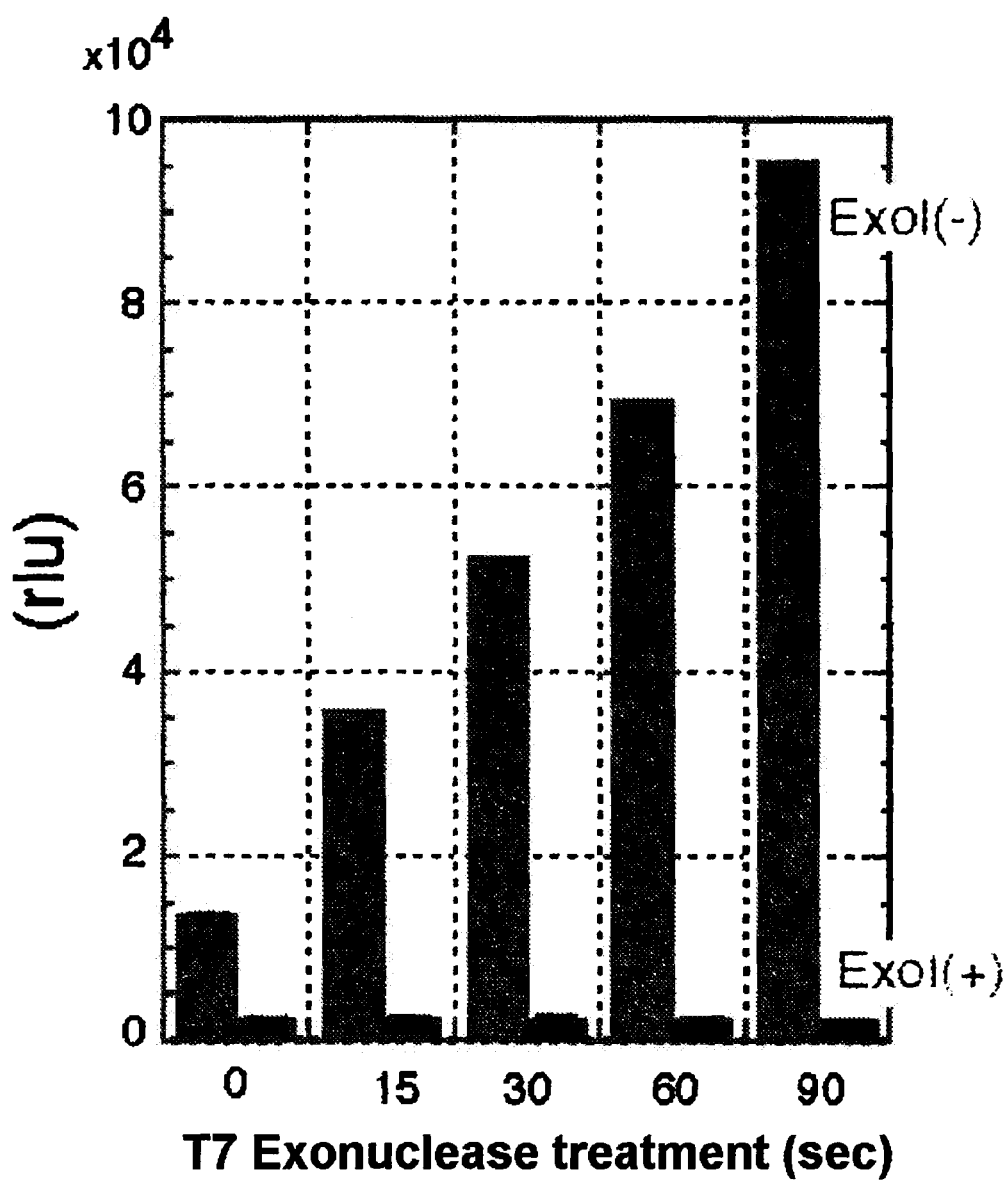
Figures 2, 6:
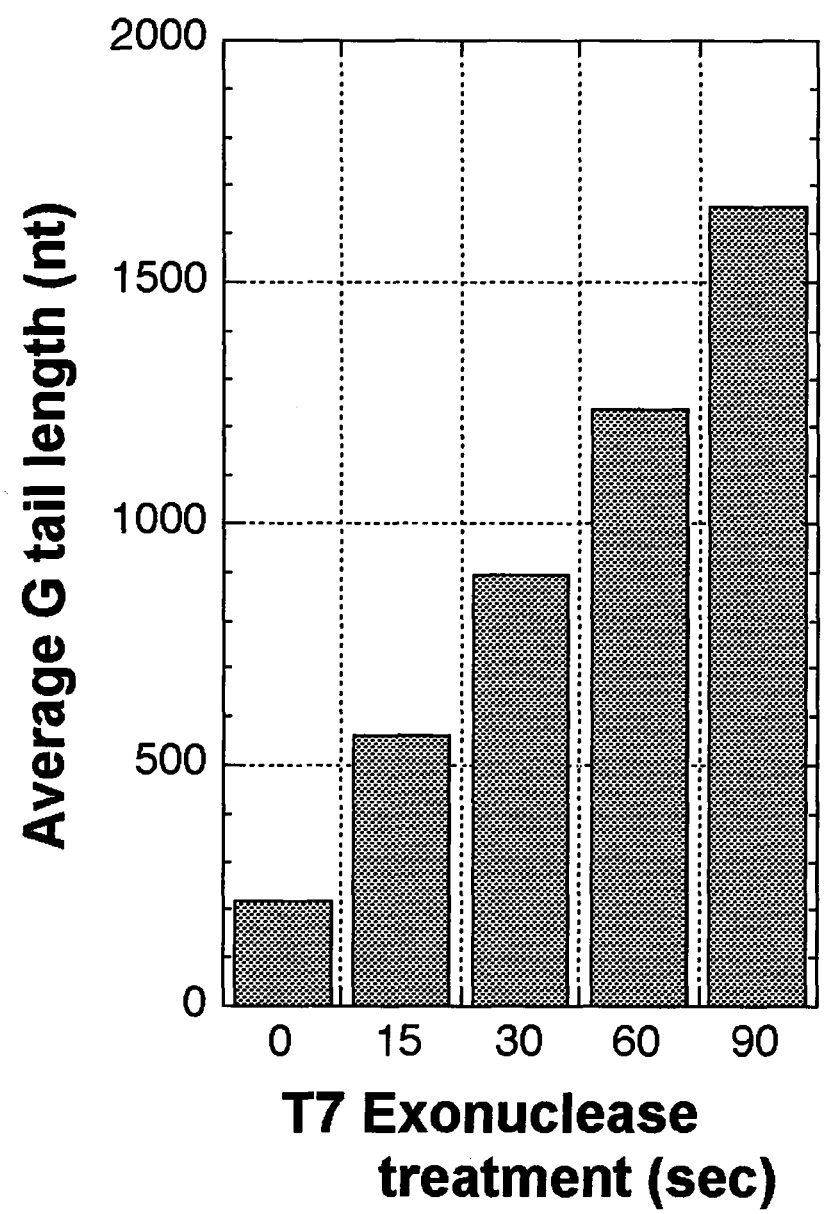

FIG. 6-1 is a graph showing the change in the amount of chemiluminescence that is dependent on the T7 exonuclease treatment period of the nondenatured DNA. The comparison of the ExoI-treated graph and the ExoI-unpretreated graph shows that an extremely large S/N ratio can be obtained.

FIG. 6-2 is a graph in which the rlu value of FIG. 6-1 is converted to an average G tail length by using the calibration curve of FIG. 2. As apparent from FIG. 6-1, the amount of chemiluminescence increased as the G tail sequence increased, in the proportion with the period of a T7 exonuclease treatment for the removal of telomere C-strand in the 5' to 3' direction.

As apparent from FIG. 6-2, the SiHa cancer cell line normally has a G tail sequence having an average length of approximately 220 nt (nt: number of nucleotides). As apparent from FIG. 6-2, the T7 exonuclease treatment of the SiHa cancer cell line-derived nondenatured genomic DNA for a period of 90 seconds until the increase of chemiluminescence resulted in the generation of a G tail having an average length of about 1600 nt.

These results show that the measuring method according to the invention can be used specifically for the measurement of the length of the G tail sequence.

<6-1> Test for Confirming the Sensitivity Limit of the Method According to the Present Invention The sensitivity limit of the measuring method according to the invention, in particular the minimum G tail length detectable, was determined, by using synthetic telomere terminal constructs (T7 TEL_Gt10, Gt20, Gt26, Gt43 and Gt62) having 10 nt, 20 nt, 26 nt, 43 nt and 62 nt G tails respectively. Synthetic telomere terminal constructs in amounts of 0.5, 1.0, 5.0 and 10 fmol were used in respective tests (measurement: twice). Synthetic telomere terminal constructs were prepared respectively by annealing DNA of SEQ ID No. 8 and DNAs of SEQ ID Nos. 9 to 13 (all, manufactured by Prorigo) and purifying the DNAs by gel electrophoresis.

T7_TEL_Gt10

(SEQ ID No. 9)
5'-TAATACgACTCACTATAgggTTAgggTTAgggTTAgggTT-3'

Gt = 10

3'-ATTATgCTgAgTgATATCCCAATCCCAATC-5'
(SEQ ID No. 8)

T7_TEL_Gt20

(SEQ ID No. 10)
5'-TAATACgACTCACTATAgggTTAgggTTAgggTTAgggTTA ggg-3' Gt = 20

3'-ATTATgCTgAgTgATATCCCAATCCCAATC-5'

T7_TEL_Gt26

(SEQ ID No. 11)
5'-TAATACgACTCACTATAgggTTAgggTTAgggTTAgggTTA gggTTAggg-3' Gt = 26

3'-ATTATgCTgAgTgATATCCCAATCCCAATC-5'

T7_TEL_Gt43

(SEQ ID No. 12)
5'-TAATACgACTCACTATAgggTTAgggTTAgggTTAgggTTAg ggTTAgggTTAgggTTAggg-3' Gt = 43

3'-ATTATgCTgAgTgATATCCCAATCCCAATC-5'

-continued

T7_TEL_Gt62

(SEQ ID No. 13)
5'-TAATACgACTCACTATAgggTTAgggTTAgggTTAgggTTA gggTTAgggTTAgggTTAgggTTAgggTTAgggTTAggg-3'

Gt = 62

3'-ATTATgCTgAgTgATATCCCAATCCCAATC-5'

The incubation and hybridization of the AE-labeled G tail HPA probe and the nondenatured DNA in the hybridization buffer for detection of G tail were performed under a condition similar to that in <4-1> above. The hydrolysis of the AE in unhybridized probe and detection of the chemiluminescence were performed under a condition similar to that in <1-2>.

<6-2> Results

Figure 7:
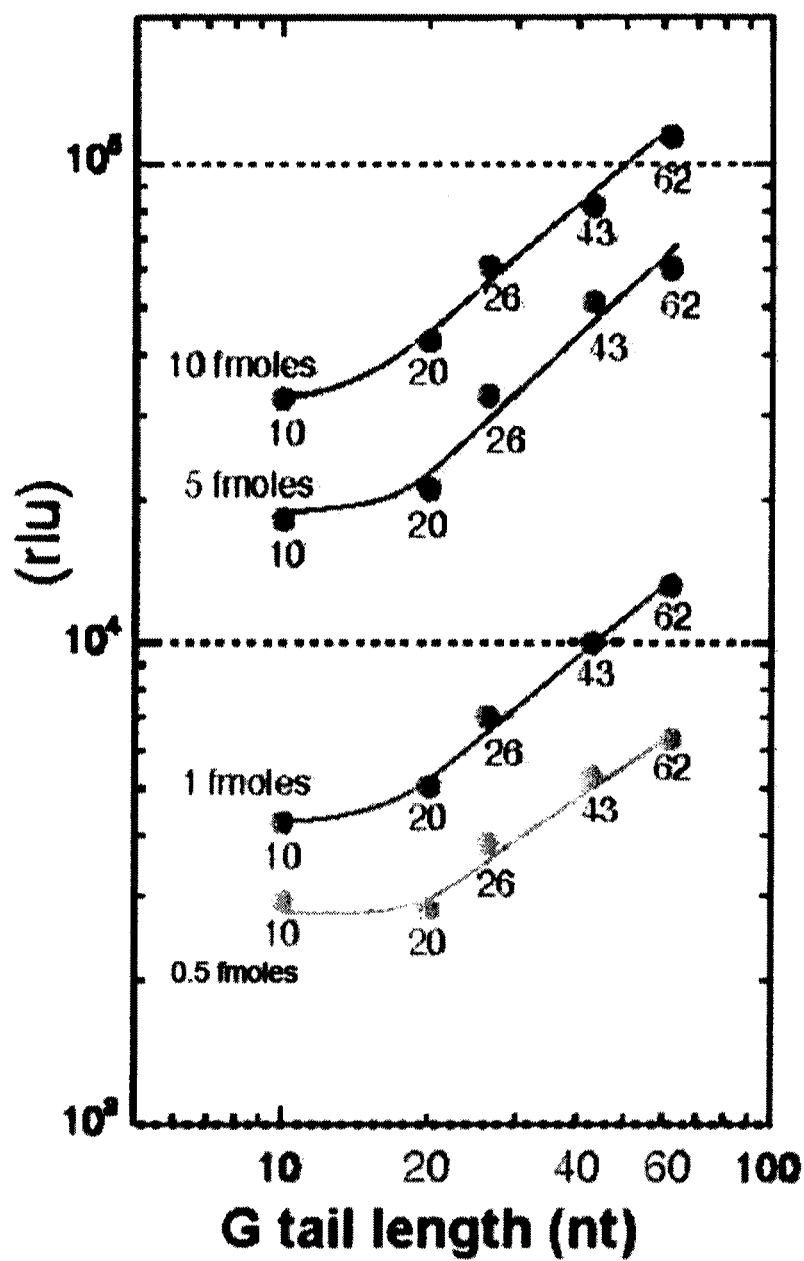
FIG. 7 is a graph showing the results of a sensitivity limit confirmation test (in particular, minimum length of a detectable G tail).

FIG. 7 is a graph showing the results of the sensitivity limit confirmation test.

As apparent from FIG. 7, when a HPA probe having a 29-base length was used, it was possible to detect a 10-nt G tail, which was smaller than the corresponding 29-base G tail DNA, but there was linearity obtained only in the G tail length range of 20 nt to 62 nt, indicating that the measuring method according to the invention can be used for quantitative measurement of G tails having a length of 20 nt or more.

<7-1> Internal Standard Test (Normalization of Total Genomic DNA Amount)

Even when the number of cells is adjusted previously before the practice of the measuring method according to the invention, it is possible to normalize the total genomic DNA amount by using the Alu DNA sequence as internal standard. For determination of the measured ratio of G tail to Alu, the nondenatured DNA used in the measurement test according to the present invention was denatured thermally and hybridized by using an Alu-HPA probe. The Alu-HPA probe used was 5'-TGTAATCCCA*GCACTTTGGGAGGC-3 (*: AE-labeled site, SEQ ID No. 2). The Alu-HPA probe was prepared by labeling the amino linker-introduced oligonucleotide (SEQ ID No. 2) prepared by using the linker-introducing reagent 3, with AE according to the method described in Japanese Patent No. 3483829.

<7-2> Results

Figure 8:
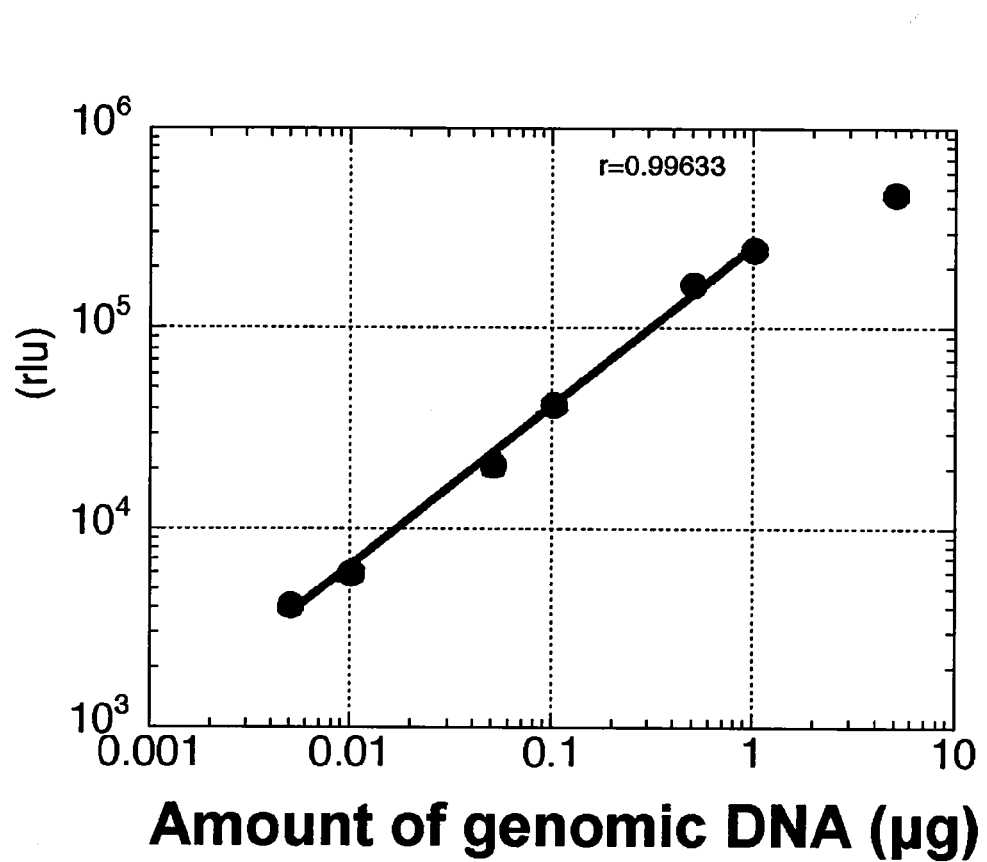
FIG. 8 is a plot of the amount of chemiluminescence in an arbitrary unit.

FIG. 8 is a plot of the amount of chemiluminescence in an arbitrary unit (measurement; thrice). As is apparent from FIG. 8, a linear response was observed in regard to the amount of chemiluminescence of the Alu DNA sequence at genomic DNA concentrations in the range of 0.005 µg to 1 µg.

Example 2

<8-1> Measurement of G Tail Sequence Length, Directly by Using Cell Pellet (1)

The SiHa cancer cell line pellet prepared in the section <8-2> below for the measurement of the length of the G tail in cell pellet was resuspended in 100 µL of the hybridization buffer above, and the suspended solution was mixed by pipetting and sheared with a 26G syringe before use. The AE-labeled G tail HPA probe in an amount of 3×10⁶ rlu and the cell pellet were incubated and hybridized under a condition similar to that in <4-1> above. Hydrolysis and chemiluminescence detection of the AE in the unhybridized probe were performed under a condition similar to that in <1-2> above. The cell pellet (1/10 volume) was denatured similarly to <7-1> above and hybridized with 3×10$^6$ rlu of the AE-labeled Alu probe, for normalization of the total genomic DNA amount.

<8-2> Preparation of Cell Pellet

A cell pellet of a SiHa cancer cell line was prepared by collecting cells after the centrifugation of the SiHa cancer cell line at 1,000 G for 5 minutes, washing the cells with cold PBS(−) twice, and freezing the cells rapidly in liquid nitrogen. The cell pellet was stored frozen at −80° C. until use.

<8-3> Results

Figure 9:
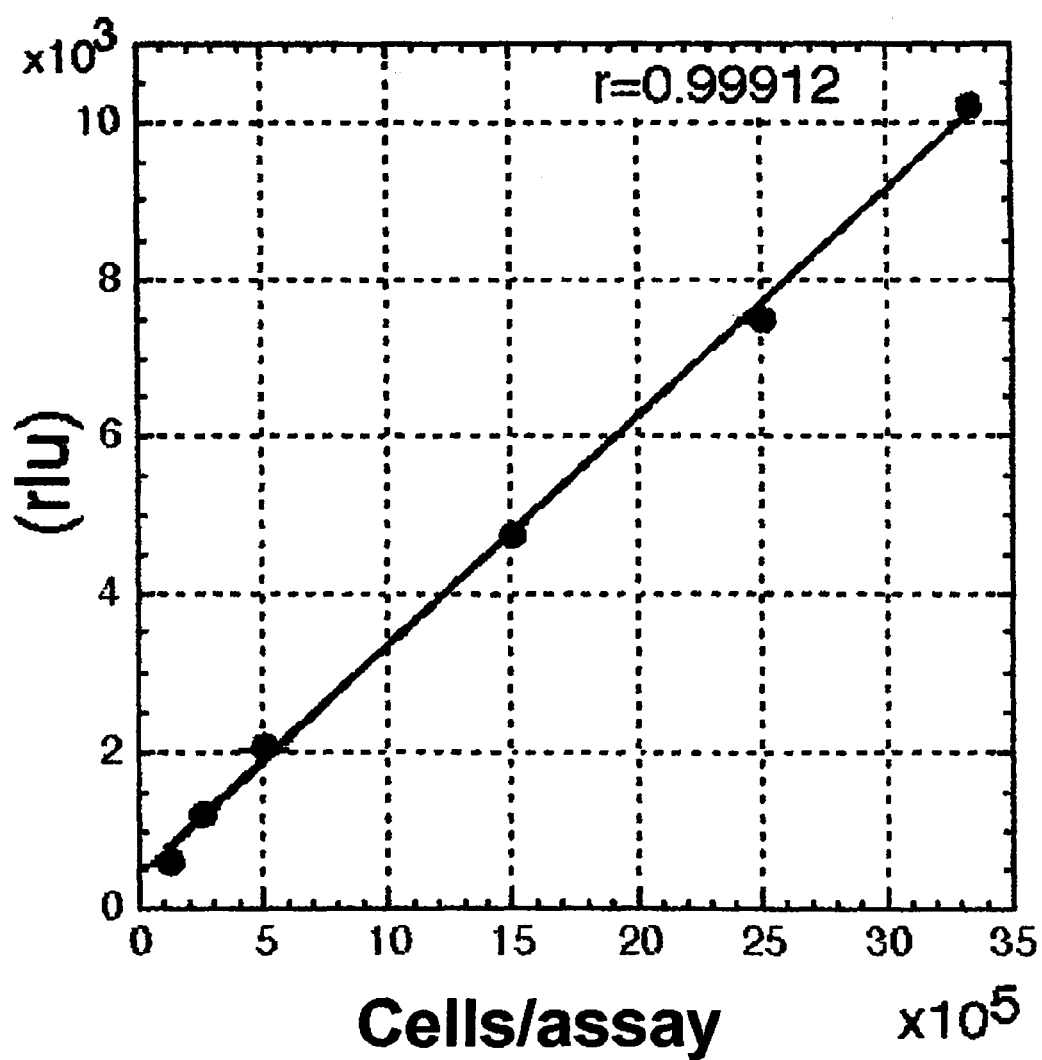
FIG. 9 is a graph showing the results when the measuring method according to the invention is applied directly to a cell pellet of a SiHa cancer cell line.

FIG. 9 is a graph showing the results when the measuring method according to the invention is applied directly to a cell pellet of a SiHa cancer cell line (measurement: twice).

When the rlu value shown in the graph of FIG. 9 is converted to the average G tail length by using the calibration curve shown in FIG. 2 above, the average G tail length of the SiHa cancer cell line was 220 nt. As apparent from FIG. 9, there was observed favorable linearity of the measuring method according to the invention in the cell concentration range of 1×10$^5$ to 3.5×10$^6$ cells, indicating that a cell pellet containing about 5×10$^5$ cells can favorably be used for G tail measurement.

<9-1> Measurement of G Tail Sequence Length, Directly by Using Cell Pellet (2)

The G tail measuring method according to the present invention was applied directly to various cell pellets (various TIG-3 human fibroblasts, various SV40-transformed cells and various SiHa cancer cells) each containing 5×10$^5$ cells; the G tail length of each cell was determined; and the biological properties of the cells were evaluated from the difference in G tail length among the cells. Each cell pellet (5×10$^5$ cells) prepared similarly to <8-2> above was resuspended in 100 μL of the hybridization-buffer, and the suspended solution was mixed by pipetting and sheared with a 26G syringe before use.

The AE-labeled G tail HPA probe in an amount of 3×10$^6$ rlu and the cell pellet were incubated and hybridized under a condition similar to that in <4-1> above. Hydrolysis and chemiluminescence detection of the AE in the unhybridized probe were performed under a condition similar to that in <1-2> above. The cell pellet (1/10 volume) was denatured similarly to <7-1> above and hybridized with 3×10$^6$ rlu of an AE-labeled Alu probe, for normalization of the total genomic DNA amount. For comparison and confirmation, the nondenatured genomic DNA was isolated from each of the cell pellets (various TIG-3 human fibroblasts, various SV40-transformed cells and various SiHa cancer cells) according to a method similar to that in <4-2>, and the measuring method according to the invention was applied to the nondenatured genomic DNA of each cell.

<9-2> Culture of the Cells Used

The following cultured cells were used in the measuring method according to the invention.

Normal human fibroblasts TIG-3, SVts9-3 (SV40-transformed TIG-3), TIG-3-hTERT (human telomerase reverse transcriptase (hTERT) cDNA-infected TIG-3), human cervical duct cancer cell line SiHa, and retrovirus packaging cell line PT67 were cultured in a Dulbecco's Modified Eagle's Medium (DMEM) supplemented with 10% fetal calf serum (manufactured by HyClone).

<9-3> Preparation of SiHa Cell Infected with Dominant Negative Allelic Gene (TRF2$^{\Delta B \Delta M}$)

Among the cells to which the measuring method according to the invention was applied, in preparation of the (TRF2$^{\Delta B \Delta M}$)-infected SiHa cell (SiHa dn TRF2), a pBabe-N-mycTRF2$^{\Delta B \Delta M}$ retrovirus construct for preparation of a retrovirus supernatant (obtained from Prof. Titia de Lange, Rockfeller University and prepared according to the method described in van Steensel B, Smogorzewska A and de Lange T., Cell, 92 (1998), 401-13) was transfected into a PT67 packaging cell line (manufactured by BD Clontech) by using a FuGene 6 transfection reagent (manufactured by Roche). After two days, the supernatant was recovered; polybrene was added to a final concentration of 6 μg/ml; and the mixture was filtered through a 0.22 μm filter (manufactured by Millipore). The filtered supernatant was used for infection to the SiHa cancer cell line. On the next day, the medium was replaced with a fresh puromycin-containing (0.5 μg/ml) complete medium, and the mixture was cultured for 4 days, to give a TRF2$^{\Delta B \Delta M}$-infected SiHa cell line.

<9-4> Results

FIG. 10a is a graph showing the results obtained when the measuring method according to the invention was applied directly to each cell pellet. Alternatively, FIG. 10b is a graph showing the results obtained when, for comparison and confirmation, the measuring method according to the invention was applied after the nondenatured genomic DNA is isolated from each cell pellet. In FIG. 10b, each right bar shows the result of G tail measurement after ExoI treatment for confirmation of telomere G tail-specific chemiluminescence, while each left bar, the result without ExoI pretreatment. In FIGS. 10a and 10b, "TIG-3(Y)" represents a young cell having a cell population doubling level (PDL) of 28; "TIG-3(S)" represents a aged cell having a PDL of 81; "TIG-3-hTERT" represents a hTERT-introduced cell; "SVts9-3 (50)" represents a young SV40-transformed cell having a PDL of 50; "SVts9-3 (121)" represents a cell in the catastrophic state having a PDL of 121; and "SiHa" represents a control vector-infected SiHa cell; and "SiHa dn TRF2" represents a dominant negative allelic gene (TRF2$^{\Delta B \Delta M}$)-infected SiHa cell.

As apparent from FIGS. 10a and 10b, the data from the cell pellets are in good agreement with those from the purified genomic DNA's. In addition, the comparison of the ExoI-treated graph and ExoI-unpretreated graph reveals that an extremely large S/N ratio is obtained. The conversion of the ordinate in each graph of FIG. 10a to the average G tail length by using the calibration curve in FIG. 2 gave the results shown in the following Table 3.

TABLE 3

Measurement of G tail length

| | | | Cell | | | | |
|---|---|---|---|---|---|---|---|
| | TIG-3 (Y) | TIG-3(S) | TIG-3-hTERT | SVts9-3 (50) | SVts9-3 (121) | SiHa | SiHa dn TRF2 |
| Average G tail length (nt) | 271 | 220 | 265 | 250 | 113 | 220 | 159 |

Figure 10:
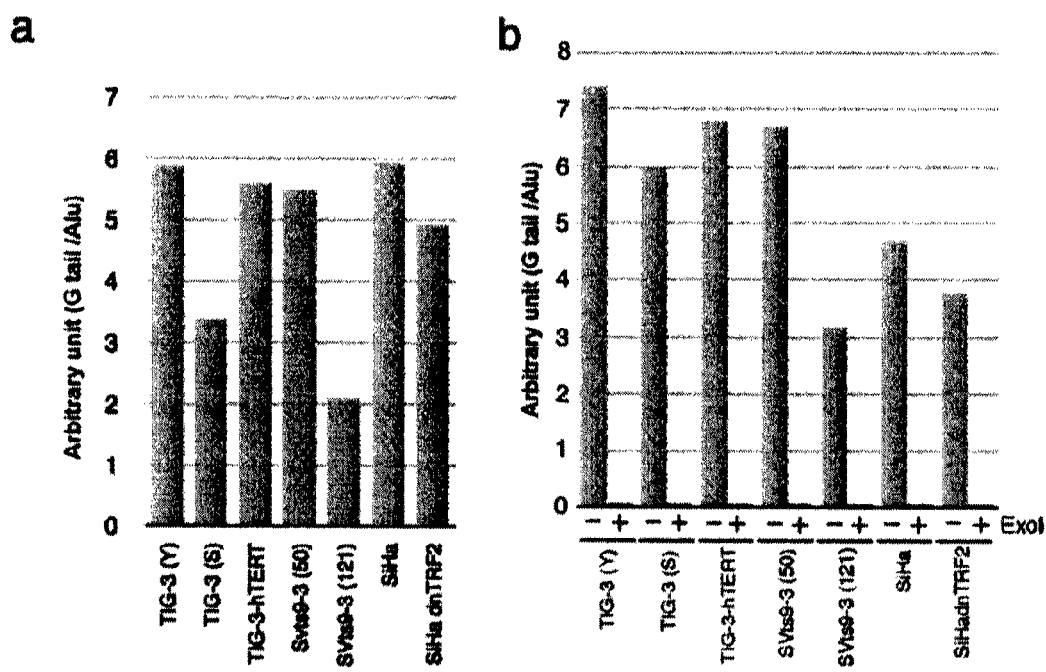
FIG. 10a is a graph showing the results obtained when the measuring method according to the invention is applied directly to each cell pellet.
FIG. 10b is a graph showing the results obtained when, for comparison and confirmation, the measuring method according to the invention is applied after an nondenatured genomic DNA is isolated from each cell pellet.

As apparent from FIG. 10 and Table 3, the average telomere G tail length was shortened especially in the SV40-transformed crisis cell, which is in good agreement with the traditional finding that the human telomere G tail shorten in the crisis stage (see, for example, Nonpatent Document 6). There was no G tail shortening observed in the hTERT-expressing TIG-3 cell. In addition, the TRF2 dominant negative allelic gene (TRF2$^{813m}$) is known to shortening of the G tail length (see, for example, Nonpatent Document 2), and the results on an SiHa cell confirmed the expected shortening of a G tail. The results above showed that the measuring method according to the invention could be used for direct measurement of G tail length by using a cell pellet and also for biological evaluation from the intercellular difference of the measured G tail length.

Example 3

<10-1> Test for Comparing the Measuring Method According to the Invention with that Described in Japanese Unexamined Patent Publication No. 2001-95586

The dominant negative allelic gene (TRF2$^{\Delta B \Delta M}$) was infected to various cells (HeLa cancer cell, SiHa cancer cell, MCF-7 cancer cell, MRC-5-hTERT normal fibroblast, and 90p normal mammary epithelial cell) according to a method similar to that in <9-3>; The nondenatured DNA was isolated from each cell (HeLa cancer cell, SiHa cancer cell, MCF-7 cancer cell, MRC-5-hTERT normal fibroblast, and 90p normal mammary epithelial cell) according to a method similar to that in <4-2>; The nondenatured DNA (5 µg) was used in the G tail measuring method according to the present invention for measurement of the G tail length; and, as a Comparative Example, the measuring method described in Japanese Unexamined Patent Publication No. 2001-95586 was applied to each denatured DNA (0.5 µg) for measurement of the entire telomere length. ExoI treatment was performed similarly to the method described in <4-3> and culture of the cells used, similarly to the method described in <9-2>.

Figure 11A:
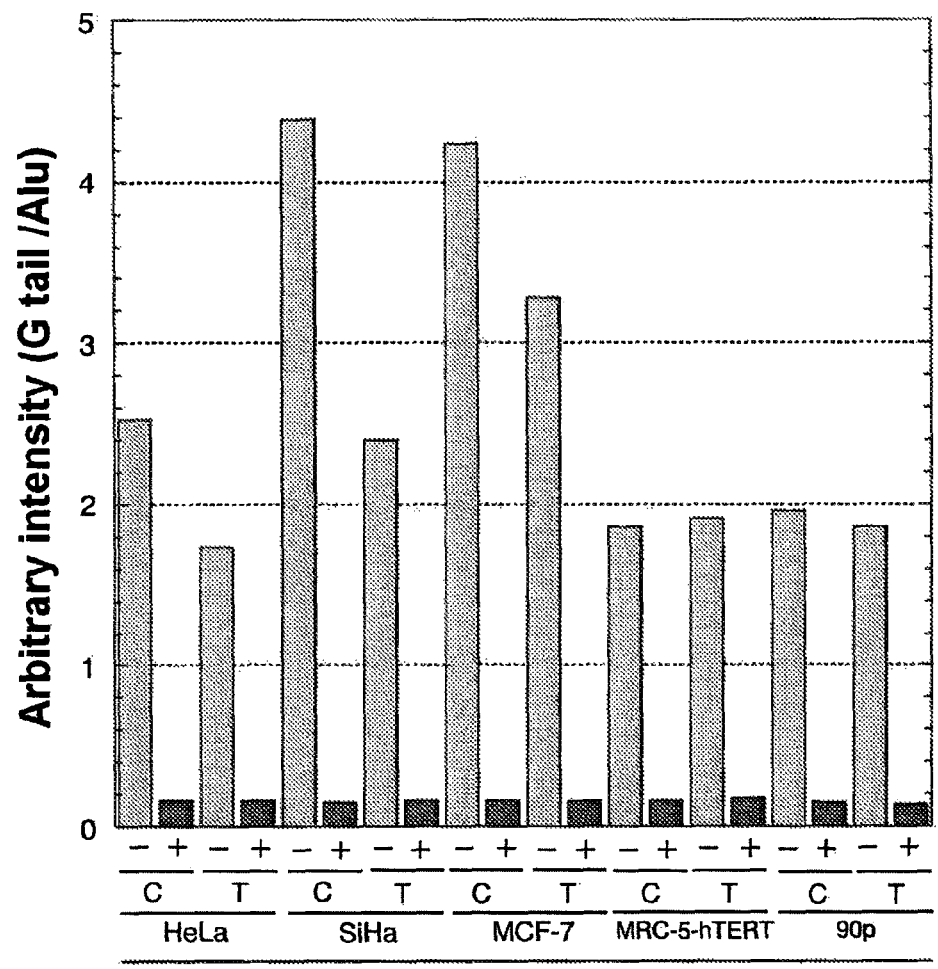
FIG. 11a is a graph showing the results of measuring a G tail by the measuring method according to the invention.
Figure 11B:
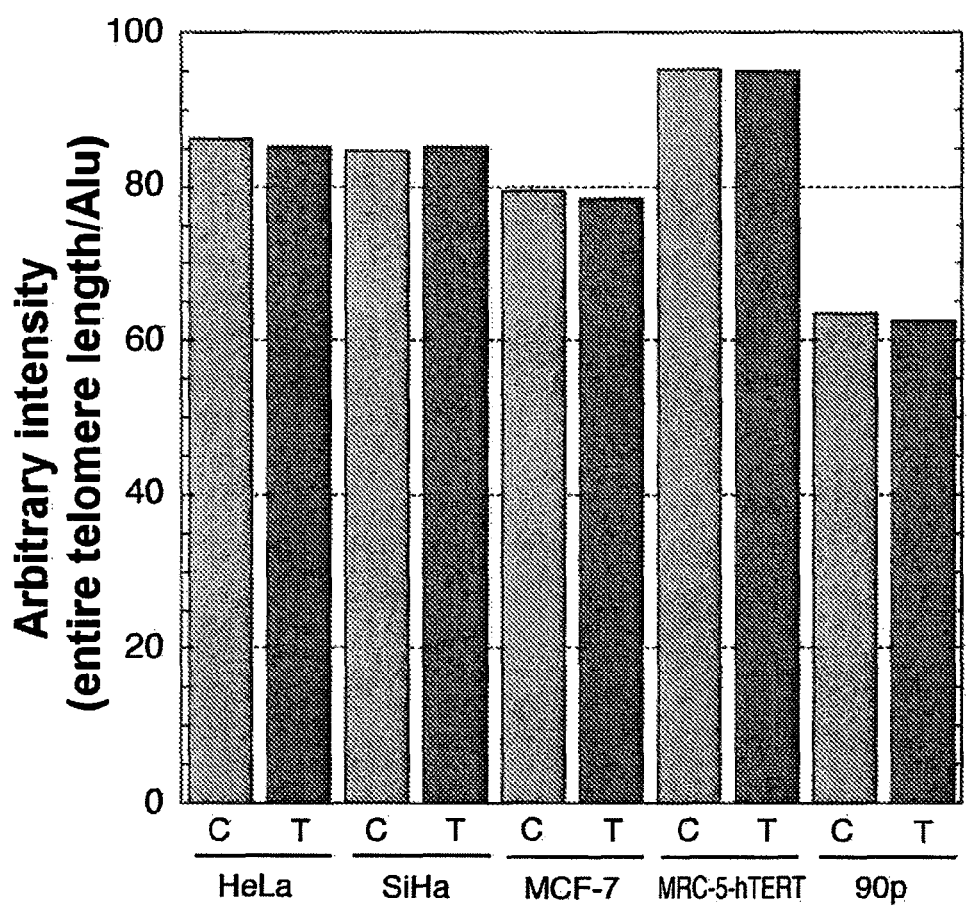
FIG. 11b is a graph showing the results of measuring the total telomere length according to the measuring method described in Japanese Unexamined Patent Publication No. 2001-95586 as a Comparative Example.

FIG. 11a is a graph showing the results of measuring G tail by the measuring method according to the invention. FIG. 11b is a graph showing the results of measuring the total telomere length by the measuring method described in Japanese Unexamined Patent Publication No. 2001-95586 as a Comparative Example. In FIG. 11a, "C" represents a control; "T" represents a cell treated with a G tail-shortening medicine telomestatin (5 µm) for 48 hours; represents a ExoI-treated cell; and − represents an untreated cell. Comparison of the ExoI-treated graph with the ExoI-unpretreated graph reveals that an extremely large S/N ratio is obtained. In FIG. 11b, "C" represents a control; and "T" represents a cell previously treated with a G tail-shortening medicine telomestatin (5 µm) for 48 hours.

First, FIGS. 11a and 11b will be described briefly. The values (arbitrary unit) on the ordinate axis were determined as the ratios of the measured luminescence intensity to the internal standard Alu sequence by using the same probe and the same instrument, and thus, FIGS. 11a and 11b can be compared and evaluated. The comparison of FIGS. 11a and 11b shows that the arbitrary intensities were approximately 2 in FIG. 11a while the arbitrary intensities about 70 in FIG. 11b, revealing that the signal intensity in FIG. 11a is only approximately 1/35 of that in FIG. 11b. Further, the nondenatured DNA was used in an amount of 5 µg in FIG. 11a, compared to 0.5 µg in FIG. 11a, and thus, the ratio is approximately 1/350 under the same concentration.

Thus apparently in the measuring method described in Patent Document 1 (Japanese Unexamined Patent Publication No. 2001-95586), the G tail length gives signal intensity only at a noise level within the range of the operation and measurement error, prohibiting G tail measurement. Then, the values on the ordinate in FIG. 11a were converted to average G tail lengths by using the calibration curve shown in FIG. 2 and the values on the ordinate in FIG. 11b to the entire telomere lengths, to give the following results shown in Table 4.

TABLE 4

G tail length and entire telomere length in various cells

| | Cell | | | | | | | | | |
|---|---|---|---|---|---|---|---|---|---|---|
| | HeLa | | SiHa | | MCF-7 | | MRC-5-hTERT | | 90p | |
| | C | T | C | T | C | T | C | T | C | T |
| Average G tail length (nt) | 126 | 89 | 220 | 121 | 212 | 162 | 96 | 96.5 | 98 | 96 |
| Entire telomere length (nt) | 4700 | 4600 | 4500 | 4600 | 4000 | 3900 | 6800 | 6750 | 3500 | 3450 |

As apparent from Table 3 and FIG. 11b, because the length of the G tail, which is 75 to 300 bases, is significantly smaller than that of the telomere having an entire length of 4 kbp to dozens kbp, even if the chromosome terminal G tail was shortened forcibly with telomestatin, for example by about 100 bases, it was not possible to observe the difference by the traditional telomere HPA method, i.e., the method described in Patent Document 1 (Japanese Unexamined Patent Publication No. 2001-95586). Alternatively as apparent from Table 3 and FIG. 11a, it was possible to detect that the G tails of the HeLa cancer cell, SiHa cancer cell, and MCF-7 cancer cell were shortened by dnTRF2 by the measuring method according to the invention, indicating that it was possible to detect a difference of 20 bases. In addition, the results show that the G tails of the MRC-5-hTERT normal fibroblast and 90p normal mammary epithelial cell were not shortened by dnTRF2.

[Example 4] Measurement of G Tail Length by Using Mouse Cultured Cell

<11-1> Isolation of Nondenatured Genomic DNA

In the present invention, the nondenatured genomic DNA may not be isolated for use, but the nondenatured genomic DNA used in the confirmation test <11-2> was previously isolated in the following manner: The nondenatured genomic DNA used for G tail length measurement was isolated from each cell line by using phenol-chloroform extraction method. Specifically, cells were centrifuged in an Eppendorf micro centrifuge tube at 6,000 rpm and 4° C. for 5 minutes, to give a pellet in the microtube. The pellet was washed once with PBS(−) and resuspended in an extraction buffer containing 10 mM Tris buffer (pH 7.6), 150 mM NaCl and NP-40, to a final concentration of 0.5%. After proteinase K digestion, phenol-chloroform extraction was performed twice. The genomic DNA was precipitated with ethanol, treated with RNase A, and then, dissolved in a TE buffer.

<11-2> Test for Confirming Nondenatured Genomic DNA Dose Response and G Tail Specificity For confirmation of nondenatured genomic DNA dose response by the measuring method according to the invention, NIH3T3 mouse fibroblast-derived nondenatured genomic DNA samples in various amounts (0.001 µg, 0.003 µg, 0.005 µg, 0.01 µg, 0.03 µg, 0.05 µg, 0.1 µg, 0.3 µg, 0.5 µg, 1 µg, 3 µg, 5 µg and 10 µg) and the AE-labeled G tail HPA probe in an amount of $3 \times 10^6$ rlu were hybridized with each other. Specifically for detection of the telomere 3'-tail (G tail) in a genomic DNA, the total amount of the DNA solution in a Falcon 352053 tube (trade name) was adjusted to 100 µL with sterile water or a TE buffer (10 mM Tris/HCl, 1 mM EDTA, pH 8.0). The mixture was heated at 65° C. in a water bath for 5 minutes; the AE-labeled G tail HPA probe in an amount of $3 \times 10^6$ rlu dissolved in 100-µL of the hybridization buffer was added to the DNA solution; and the mixture was stirred thoroughly with a Vortex mixer and incubated at 60° C. for 20 minutes. Hydrolysis of the AE in unhybridized probe and detection of the chemiluminescence were performed under a condition similar to that in <1-2>.

<11-3> Results

Figure 12:
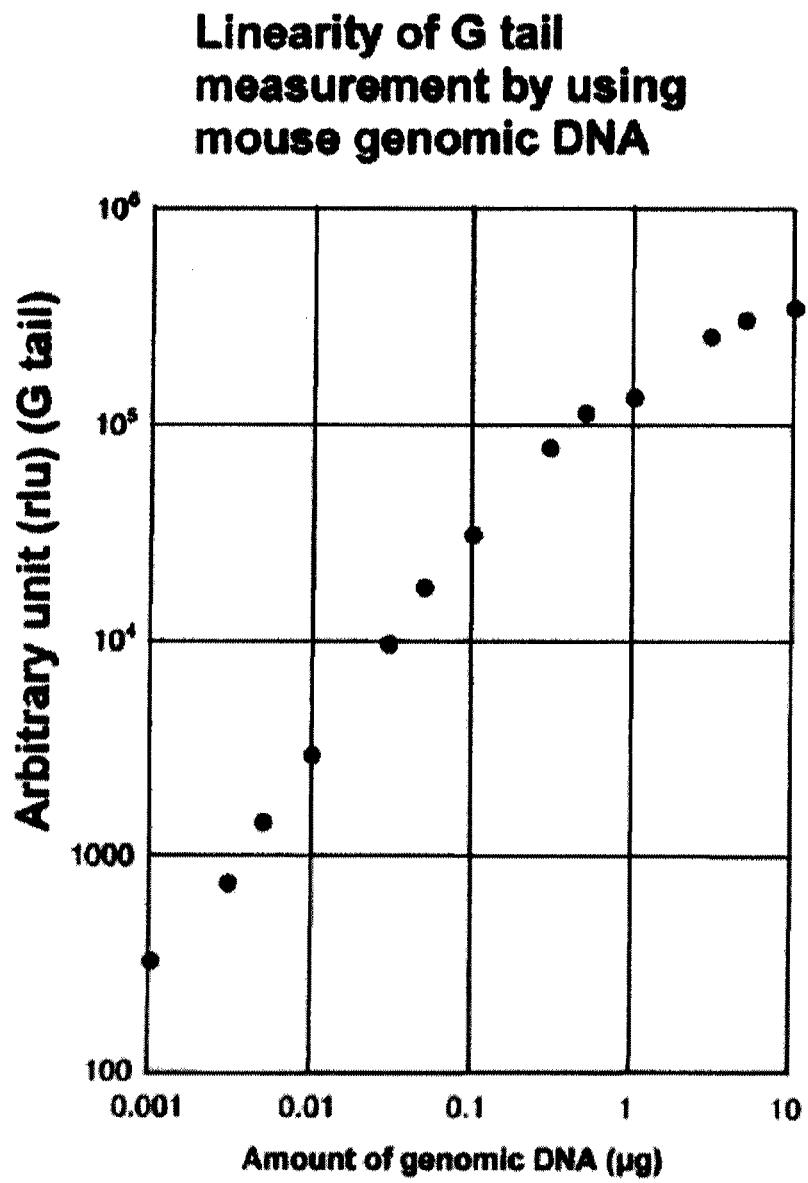
FIG. 12 is a graph showing the linearity in the measurement of G tail length by using a mouse genomic DNA.

As apparent from FIG. 12, there was a linear response at the nondenatured genomic DNA concentration in the range of 0.001 µg to 10 µg. The results indicate that 0.01 µg of the nondenatured genomic DNA may be used normally.

<12-1>

Measurement of G tail length by using mouse tissue

Genomic DNAs were isolated from mouse tissues of organs such as liver, kidney, stomach, large intestine, and thymus, and 1 µg to 5 µg of the genomic DNAs were used for G tail measurement.

<12-2> Isolation of Nondenatured Genomic DNA

In the present invention, the nondenatured genomic DNA may not be isolated for use, but the nondenatured genomic DNA used in the confirmation test <12-1> was previously isolated in the following manner: The nondenatured genomic DNA used for G tail length measurement was isolated from each tissue by using phenol-chloroform extraction method. Specifically, each tissue, which was stored frozen at –80° C., was thawed, homogenized immediately, and resuspended in an extraction buffer containing 10 mM of Tris buffer (pH 7.6), 150 mM of NaCl, and NP-40, to a final concentration of 0.5%. After proteinase K digestion, phenol-chloroform extraction was performed twice. The genomic DNA was precipitated with ethanol, treated with RNase A, and then, dissolved in a TE buffer.

<12-3> Test for Confirming Nondenatured Genomic DNA Dose Response and G Tail Specificity For the confirmation of the nondenatured genomic DNA dose response by the measuring method according to the invention, 0.5 µg of nondenatured genomic DNAs derived from various mouse tissues and the AE-labeled G tail HPA probe in an amount of $3 \times 10^6$ rlu were hybridized with each other. Specifically for detection of the telomere 3'-tail (G tail) in the genomic DNA, the total amount of the DNA solution in a Falcon 352053 tube (trade name) was adjusted to 100 µL with sterile water or a TE buffer (10 mM Tris/HCl, 1 mM EDTA, pH 8.0). The mixture was heated at 65° C. in a water bath for 5 minutes; the AE-labeled G tail HPA probe in an amount of $3 \times 10^6$ rlu dissolved in 100-µL of the hybridization buffer was added to the DNA solution; and the mixture was stirred thoroughly with a Vortex mixer and incubated at 60° C. for 20 minutes. Hydrolysis of the AE in unhybridized probe and detection of the chemiluminescence were performed under a condition similar to that in <1-2>.

<12-4> Results

Figure 13:
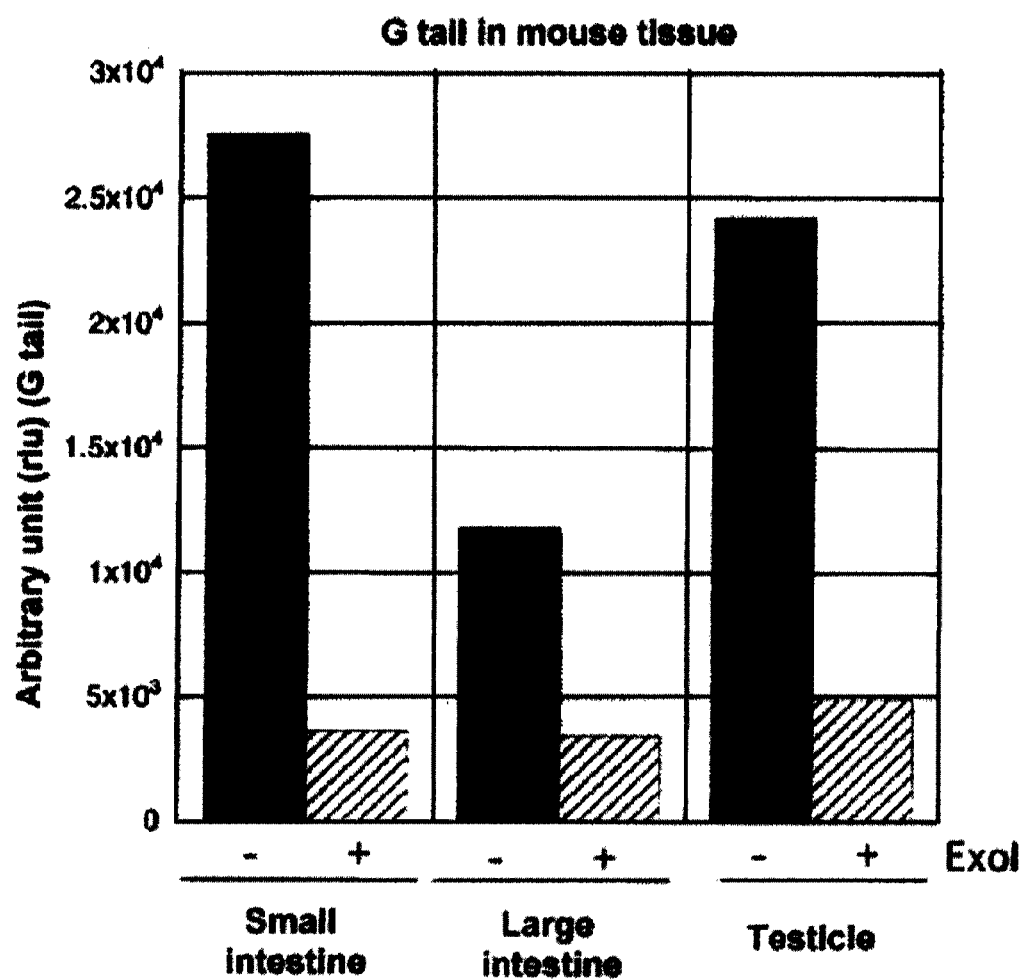
FIG. 13 is a graph showing G tail lengths observed in mouse tissues.

It was possible to detect G tail signals by the present measuring method in various tissues of small intestine, large intestine, testicle, and the like. Relatively longer G tails were detected in small intestine and testicle, while the G tail in large intestine was shorter. FIG. 13 shows that all samples were ExoI-sensitive which confirmed that the detected chemiluminescence was specific to the single-stranded G tail, while the comparison of the ExoI-treated graph and the ExoI-unpretreated graph shows that it is possible to measure the G tail sufficiently also in mouse tissues.

<13-1> Internal Standard Test by Using Mouse (Normalization of Total Genomic DNA Amount)

It is possible to normalize the total mouse genomic DNA amount by using a repeated sequence A1 or B2 present in mouse as an internal standard, even when the cell number is adjusted before the measuring method according to the invention is carried out. For determination of the measurement ratio of the G tail to A1, A2 or B2, the nondenatured DNA used in the measurement test according to the present invention was denatured thermally and hybridized by using an A1, A2 or B2-HPA probe. The A1, A2 or B2-HPA probe used was Ala probe: 5'-GAA CAG TGT ATA T*C AAT GAG TTA CAA T-3' (SEQ ID No. 14); A1b probe: 5'-GAA CAG TGT ATA TCA A*T GAG TTA CAA T-3' (SEQ ID No. 15); A2a probe: 5'-CGT TGG AA*ACG GGA TTT GTA GAA CA-3' (SEQ ID No. 16); A2b probe: 5'-CGT TGG AAA CGG GA*TTT GTA GAA CA-3' (SEQ ID No. 17); B2_1b probe: 5'-GTC TGA AGA CA*GCT ACA GTG TA-3' (SEQ ID No. 18); B2-2a probe: 5'-CCG ACT G*C TCT TCT GAA GGT C-3' (SEQ ID No. 19); or B2_2b probe: 5'-CCG ACT GCT CTT C*T GAAGGT C-3' (SEQ ID No, 20) (in sequences above, "*" represents the AE-labeling site).

The A1, A2 or B1-HPA probe was prepared by labeling the amino linker-introduced oligonucleotide (SEQ ID No. 2) prepared by using the linker-introducing reagent 3 according to the method described in Japanese Patent No. 3483829 with AE.

<13-2> Results

Figures 1, 14:
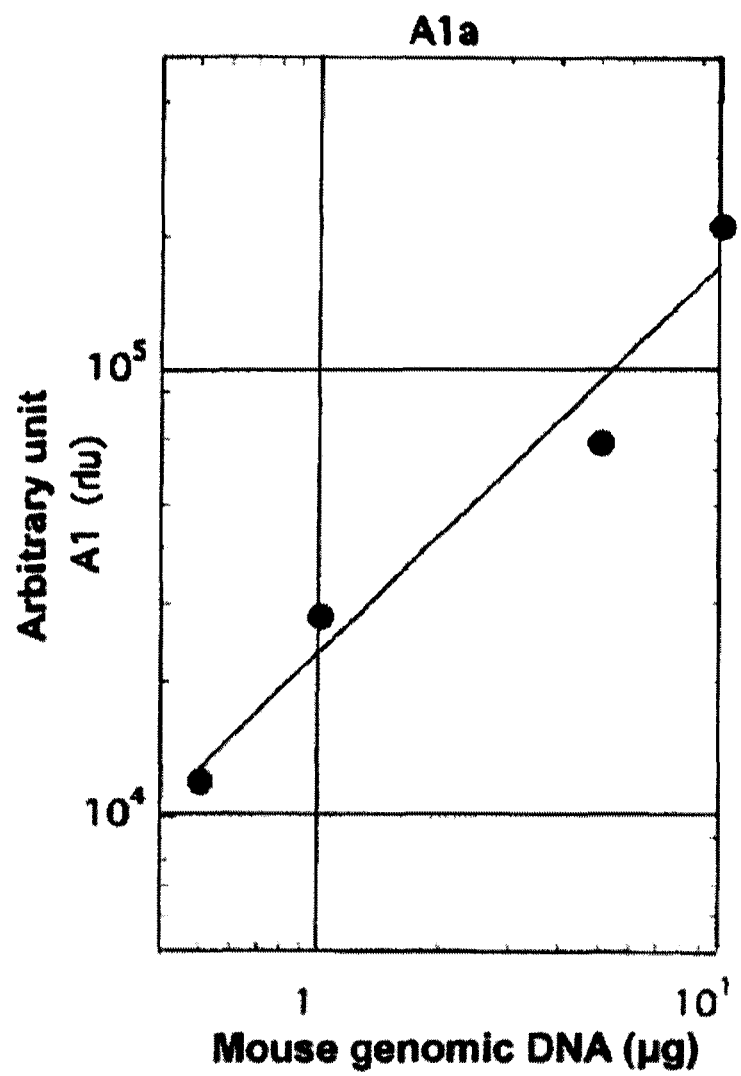
Figures 2, 14:
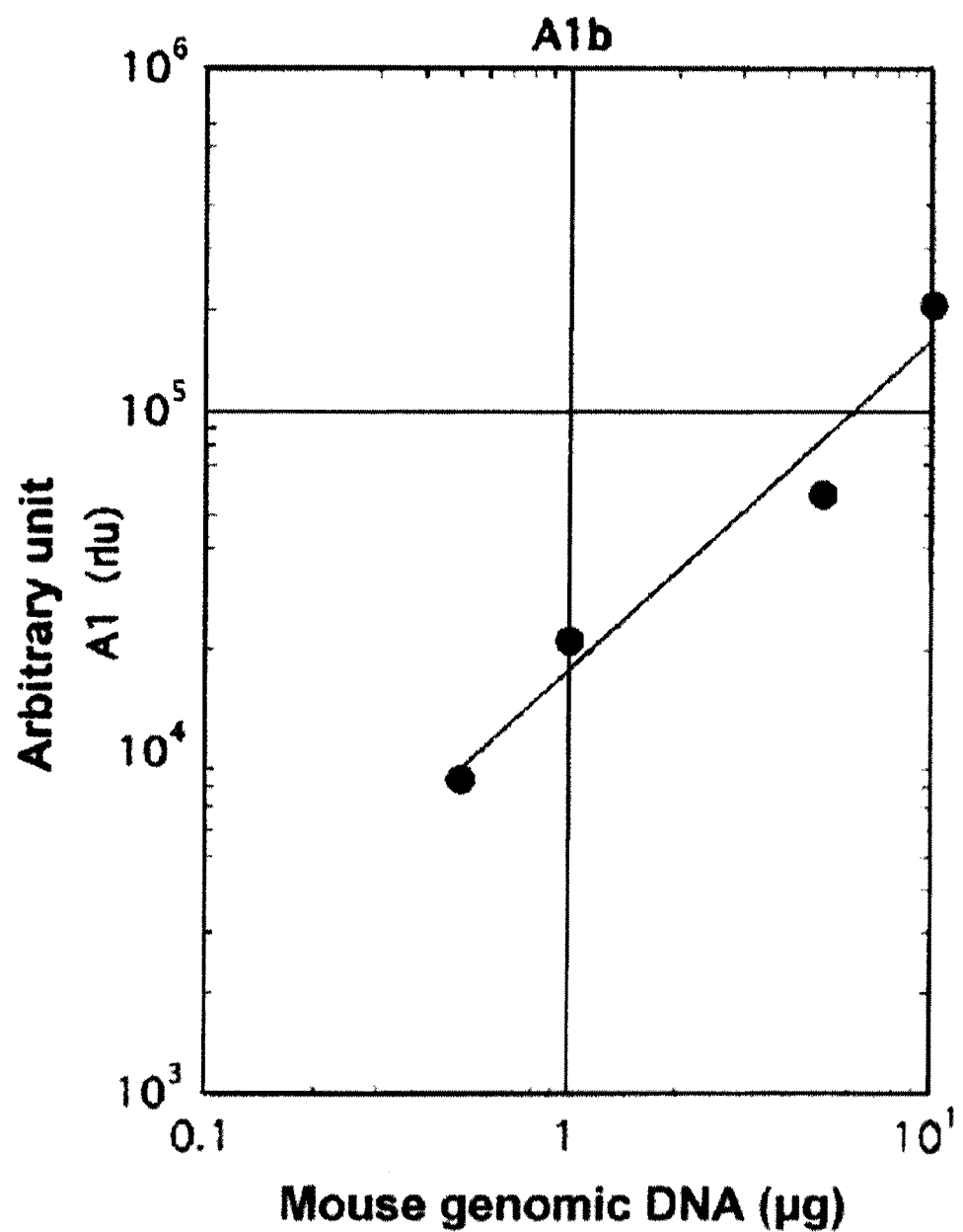
Figures 3, 14:
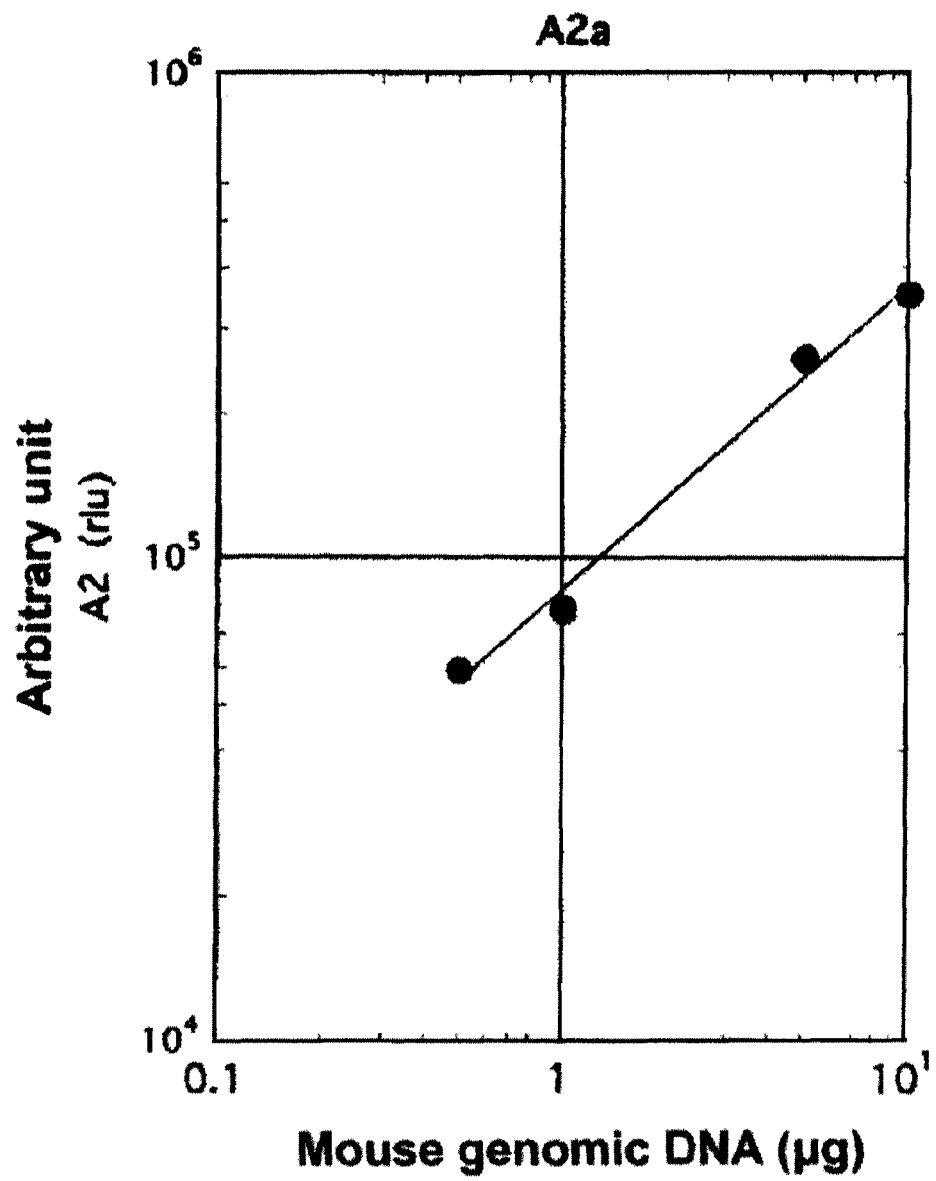
Figures 4, 14:
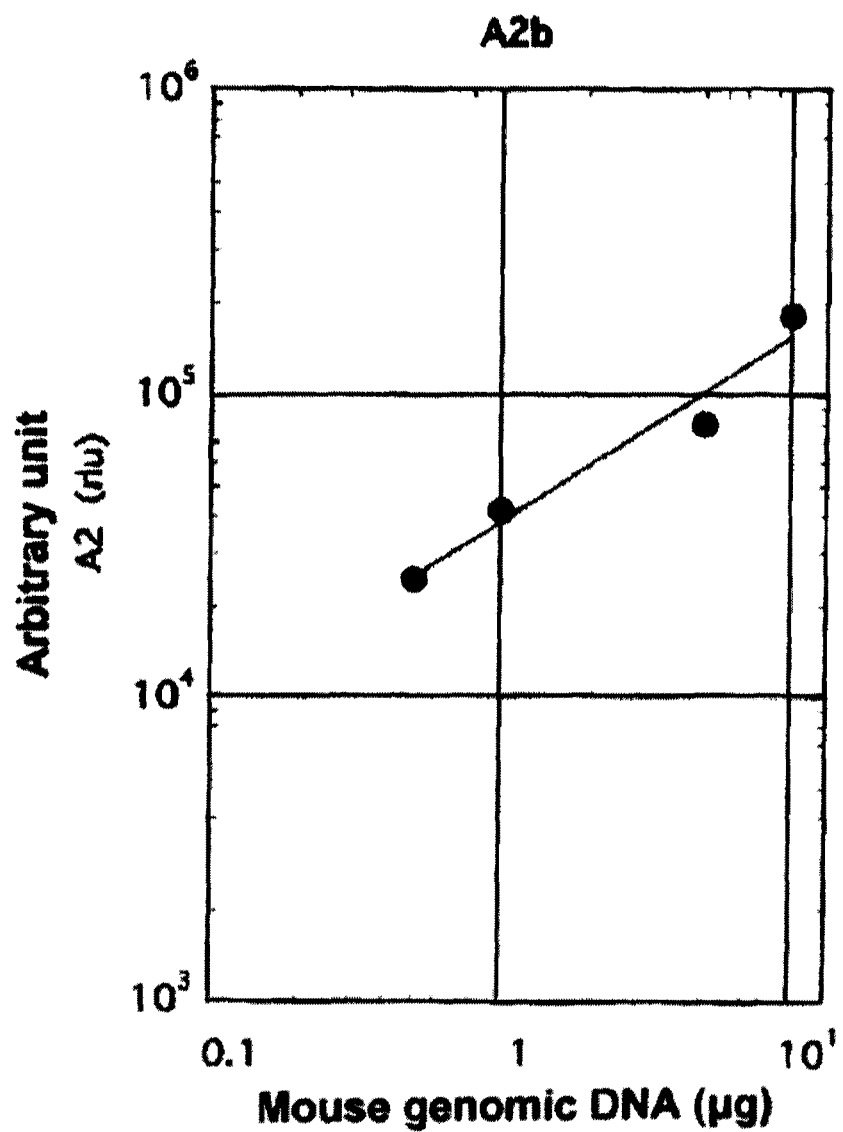
Figures 5, 14:
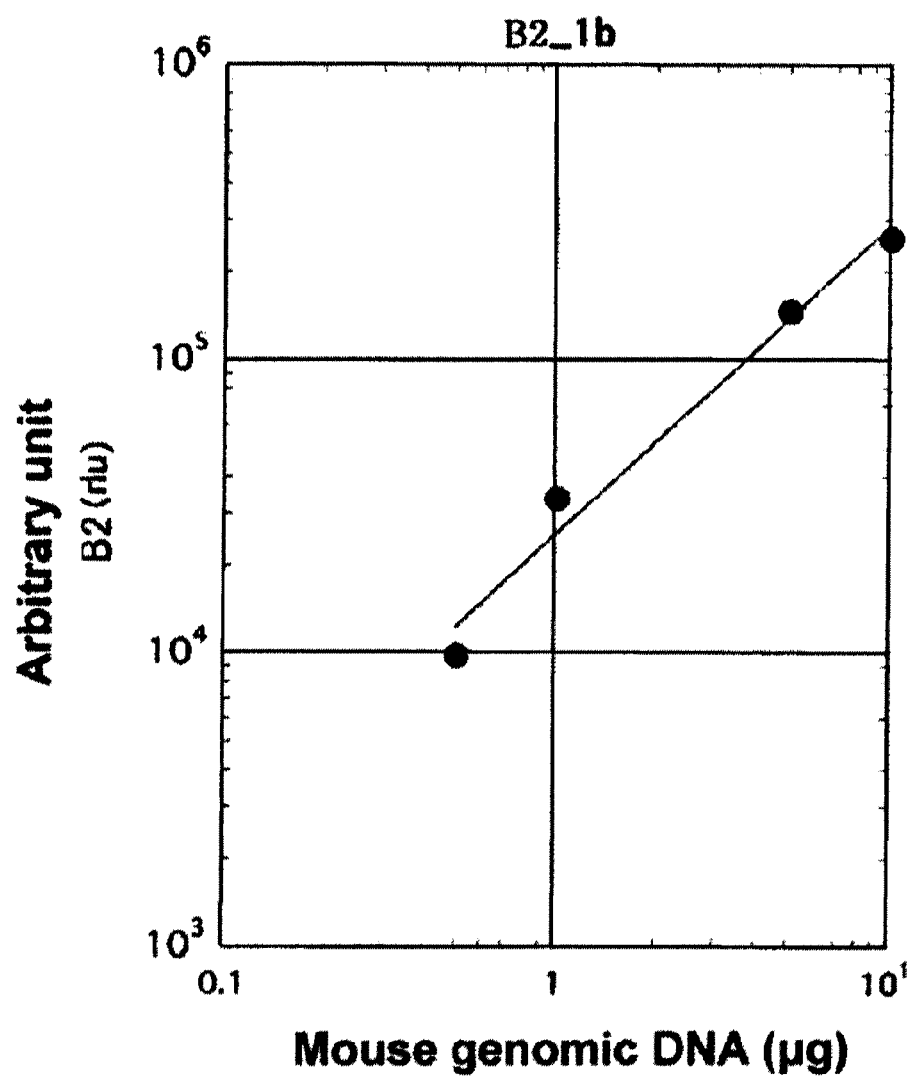
Figures 6, 14:
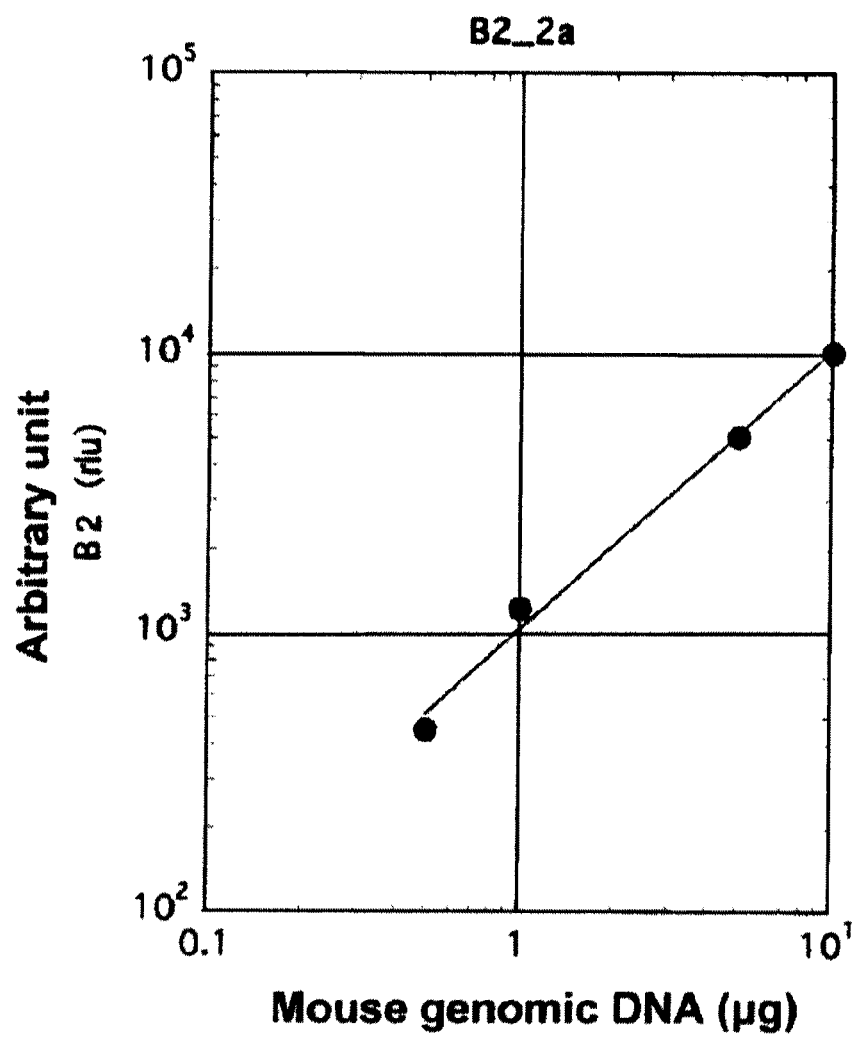
Figures 7, 14:
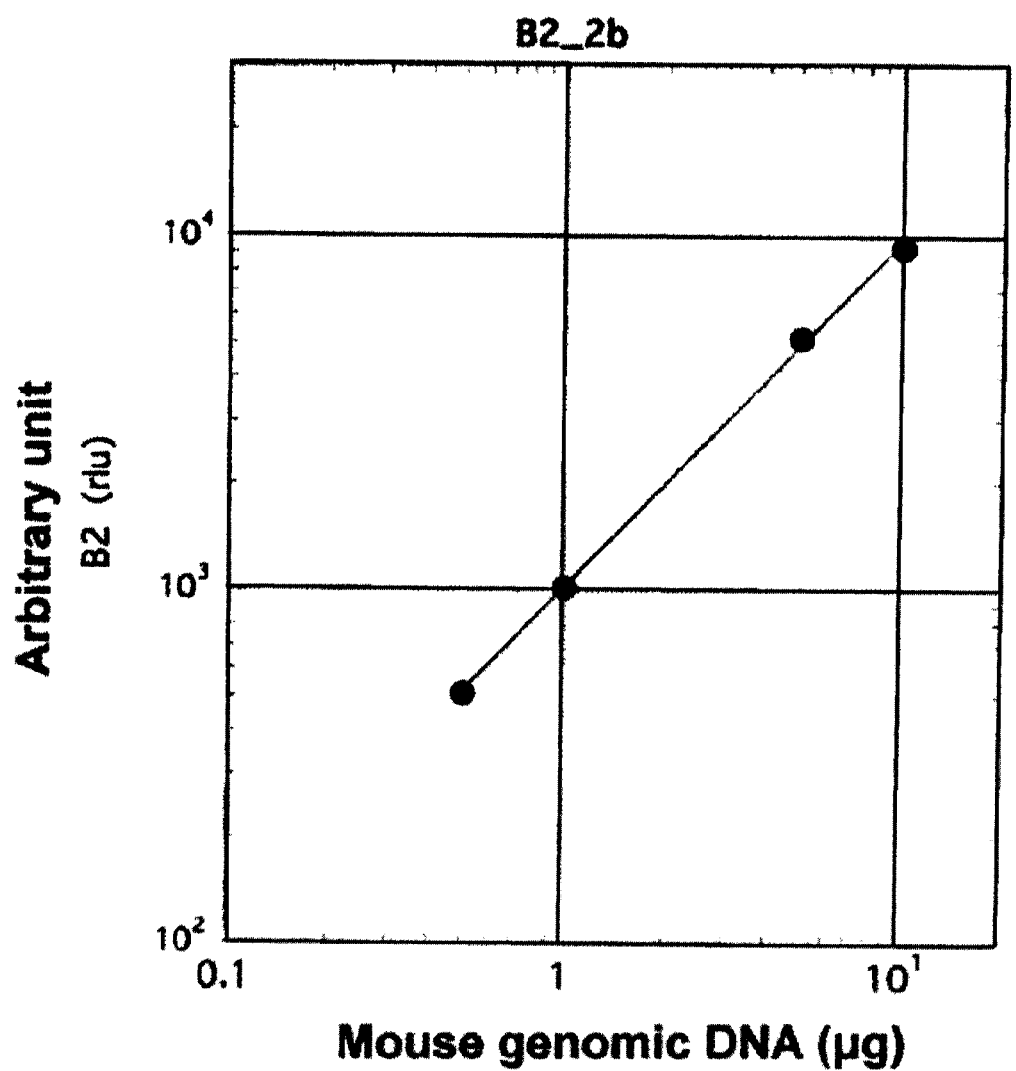

FIGS. 14-1 to 14-7 are plots of the amount of chemiluminescence in an arbitrary unit (measurement: thrice). As apparent from FIGS. 14-1 to 14-7, it was possible to obtain linear response in chemiluminescence by the A1, A2 or B2 DNA sequence in the genomic DNA concentration range of 0.5 µg to 10 µg.

[Example 5] Measurement of G Tail Length by Using a 96-Well Plate

<14-1> Test for Confirming Synthetic Single-Stranded G Tail Dose-Response Relationship by Using a 96-Multi-Well Plate For the confirmation of dose-response relationship by the measuring method according to the invention, the following hybridization buffer diluents (30 µL) containing a synthetic single-stranded G tail, 84 bases, 5'-(TTAGGG)$_{14}$-3' (manufactured by Prorigo) at various concentrations and an AE-labeled G tail HPA probe (5'-CCCTAACCCTAACC*CTAACCCTAACCCTA-3', SEQ ID No. 1, *AE-labeling site, 29 bases), having a amount of chemiluminescence of $3 \times 10^6$ relative light units (hereinafter, referred to simply as rlu), were incubated and allowed to hybridize with each other in 30 µL of the following hybridization buffer described in Example 1 <1-1> at 70° C. for 30 minutes, for example, in Thermomixer Comfort (manufactured by Eppendorf). The temperature and the period may be modified according to the apparatus used.

The AE-labeled G tail probe was prepared by labeling the amino linker-introduced oligonucleotide (SEQ ID No. 1) prepared by using the linker-introducing reagent 3, with AE according to the method described in Japanese Patent No. 3483829.

<14-2> Hydrolysis of Unhybridized Probe and Chemiluminescence Detection

The hydrolysis of the AE in the unhybridized probe was performed by charging 90 μL of a hydrolysis buffer (0.6 mol/L tetrasodium borate buffer containing 50 mL IL of Triton X-100, pH 8.5) into each reaction tube, stirring the mixture thoroughly, and incubating the mixture at 70° C. for 25 minutes on a plate block heater. The AE in hybridized probe was not hydrolyzed under the condition. These tubes were left at room temperature for about 2 minutes; in a 96-well-plate-compatible luminometer (allowing simultaneous addition of two reagents, GloMax (trade name) 96 Microplate Luminometer w/Dual Injectors (trade name), manufactured by Promega), 60 μL of a reader I solution was added thereto; 60 μL of a reader II solution was added additionally after two seconds; and the chemiluminescence was measure for a measuring period of 2 seconds.

<14-3> Results

Figure 15:
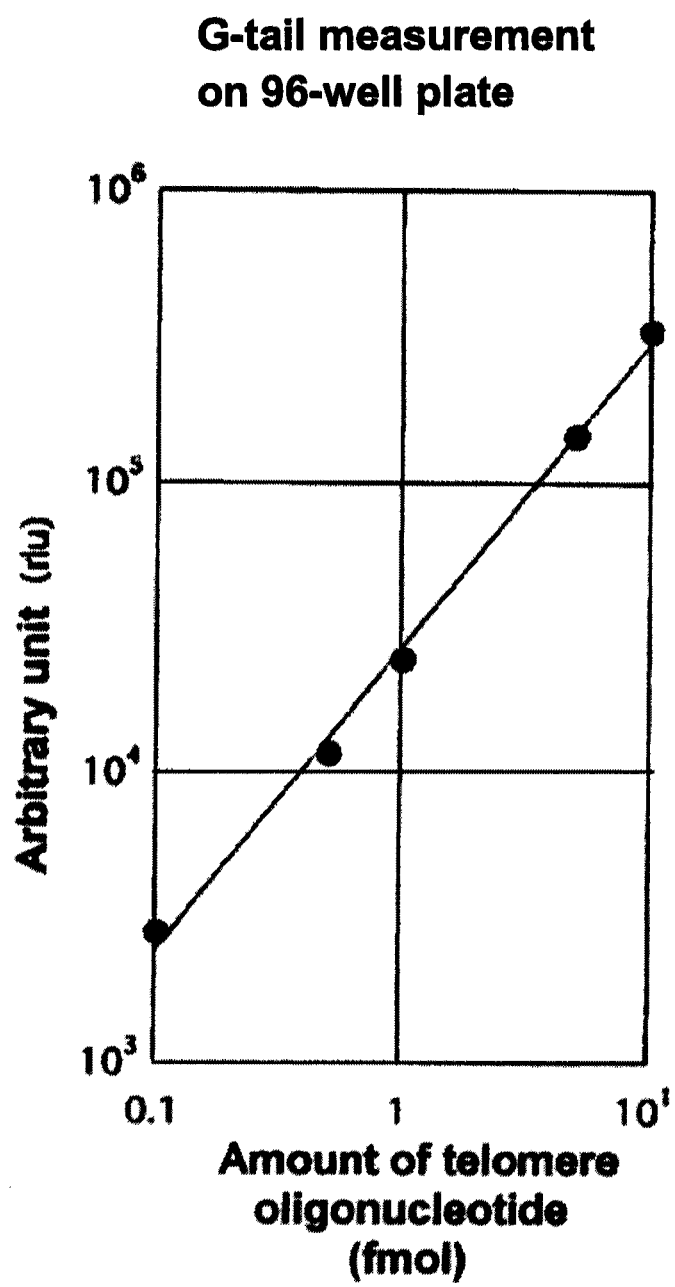
FIG. 15 is a graph showing the results of measuring the responsiveness of an AH-labeled G tail HPA probe and a single-stranded synthetic G tail on a 96-well plate.

FIG. 15 is a graph showing the results of a dose-response test on G tail measurement carried out on a 96-well plate by using the 29-base AE-labeled G tail HPA probe and the single-stranded synthetic 84-base G tail. As apparent from FIG. 15, the signal intensity increased linearly as the increase in oligonucleotide dosage in the range of 0.05 fmol to 10 fmol.

INDUSTRIAL APPLICABILITY

The present invention provides a method of measuring the length of the sequence of the telomere single-stranded tail (G tail) specifically and rapidly at high sensitivity without tedious processing operation and denaturation and a kit for use therein.

The kit according to the present invention is useful as a test reagent for patients with various diseases relevant to cancer and aging, which are regarded as diseases associated with G tail loss. It is also useful for use in basic physiological research on diseases associated with aging, cancer, and telomere abnormality.

The present invention has been described with reference to its favorable embodiments, but the description above is not aimed at restricting the invention in any way unless specified otherwise, and the invention should be construed widely in the spirit and the scope of the invention specified by the Claims attached.

The invention claimed is:

1. A method of determining the average length of a human G tail sequence in a nondenatured chromosomal DNA sample, comprising:

receiving a nondenatured chromosomal DNA sample from a human sample containing $1 \times 10^5$ to $3.5 \times 10^6$ cells, the nondenatured chromosomal DNA having a G tail sequence;

receiving a G tail probe, the G tail probe having a label which can emit chemiluminescence and also having a base sequence consisting of $(CCCTAA)_n$, where n is an integer of 1 to 10, the base sequence being complementary to a telomere repeat sequence;

hybridizing the G tail sequence in the nondenatured chromosomal DNA sample with the G tail probe, resulting in (A) a hybridized G tail probe that is hybridized to the G tail sequence and (B) an unhybridized G tail probe that is not hybridized to the G tail sequence;

hydrolyzing the label in the unhybridized G tail probe;

measuring the chemiluminescence from the hybridized G tail probe in relative light units (rlu) and generating a value of the chemiluminescence from the hybridized G tail probe;

selectively removing single-stranded nucleotide in the 3' to 5' direction from the hybridized G tail sequence in the nondenatured chromosomal DNA sample using an exonuclease to confirm that the chemiluminescence from the hybridized G tail probe is specific to the G tail sequence;

hybridizing Alu repeats in the chromosomal DNA in the nondenatured chromosomal DNA sample with an Alu probe that has a label which can emit chemiluminescence, resulting in a hybridized Alu probe;

measuring the chemiluminescence from the hybridized Alu probe in relative light units (rlu) and generating a value of the chemiluminescence from the hybridized Alu probe;

converting the value of the chemiluminescence from the hybridized Alu probe to an amount of the chromosomal DNA in the nondenatured chromosomal DNA sample using a first calibration curve;

converting the value of the chemiluminescence from the hybridized G tail probe to an amount of the G tail sequence in the nondenatured chromosomal DNA sample using a second calibration curve; and determining the average length of the G tail sequence based on the ratio of the amount of the G tail sequence to the amount of the chromosomal DNA in the nondenatured chromosomal DNA sample;

wherein the length of the G tail sequence is up to 1600 nucleotides.

2. The method according to claim 1, wherein the human sample is a cell pellet of blood, a cultured cell, a fresh tissue, a cryopreserved tissue or a formalin-fixed tissue.

3. The method according to claim 2, wherein the label is an acridinium ester, luminol, isoluminol, pyrogallol, protohemin, aminobutylethyl-n-isoluminol or aminohexylethyl-n-ethyl-isoluminol.

4. The method according to claim 1, wherein the exonuclease is an exonuclease I.

5. The method according to claim 1, wherein the label is an acridinium ester, luminol, isoluminol, pyrogallol, protohemin, aminobutylethyl-n-isoluminol or aminohexylethyl-n-ethyl-isoluminol.

6. The method of claim 1, wherein the human sample is a cell pellet and is dissolved in a hybridization buffer.

7. A method of determining the average length of a human G tail sequence in a nondenatured chromosomal DNA sample, comprising:
- receiving a nondenatured chromosomal DNA sample from a human sample containing $1 \times 10^5$ to $3.5 \times 10^6$ cells, the nondenatured chromosomal DNA having a G tail sequence;
- receiving a G tail probe, the G tail probe having a label which can emit chemiluminescence and also having a base sequence consisting of (CCCTAA)n, where n is an integer of 1 to 10, the base sequence being complementary to a telomere repeat sequence;
- hybridizing the nondenatured chromosomal DNA sample with the G tail probe, resulting in (A) a hybridized G tail probe that is hybridized to the G tail sequence and (B) an unhybridized G tail probe;
- hydrolyzing the label in the unhybridized G tail probe;
- measuring the chemiluminescence from the hybridized G tail probe in relative light units (rlu) and generating a value of the chemiluminescence from the hybridized G tail probe;
- converting the value of the chemiluminescence from the hybridized G tail probe to an amount of G tail sequence in the nondenatured chromosomal DNA sample using a calibration curve generated by hybridizing G tail oligomer standards with the G tail probe;
- determining the amount of chromosomal DNA in the nondenatured chromosomal DNA sample by measuring an amount of Alu repeats in the nondenatured chromosomal DNA sample and converting the amount of Alu repeats in the nondenatured chromosomal DNA to an amount of the chromosomal DNA in the nondenatured chromosomal DNA sample using a calibration curve; and
- determining the average length of the G tail sequence based on the amount of the G tail sequence and the amount of chromosomal DNA in the nondenatured chromosomal DNA sample;
- wherein the length of the G tail sequence is up to 1600 nucleotides.

8. The method according to claim 1, wherein the human sample is a cell pellet of blood, a cultured cell, a fresh tissue, a cryopreserved tissue or a formalin-fixed tissue.

9. The method according to claim 8, wherein the label is an acridinium ester, luminol, isoluminol, pyrogallol, protohemin, aminobutylethyl-n-isoluminol or aminohexylethyl-n-ethyl-isoluminol.

10. The method according to claim 7, wherein the label is an acridinium ester, luminol, isoluminol, pyrogallol, protohemin, aminobutylethyl-n-isoluminol or aminohexylethyl-n-ethyl-isoluminol.

11. The method of claim 7, wherein the human sample is a cell pellet and is dissolved in a hybridization buffer.

* * * * *

SEQUENCE LISTING

```
<160> NUMBER OF SEQ ID NOS: 20

<210> SEQ ID NO 1
<211> LENGTH: 29
<212> TYPE: DNA
<213> ORGANISM: Artificial
<220> FEATURE:
<223> OTHER INFORMATION: G-tail probe

<400> SEQUENCE: 1
ccctaaccct aaccctaacc ctaacccta                                    29

<210> SEQ ID NO 2
<211> LENGTH: 24
<212> TYPE: DNA
<213> ORGANISM: Artificial
<220> FEATURE:
<223> OTHER INFORMATION: Alu-probe

<400> SEQUENCE: 2
tgtaatccca gcactttggg aggc                                         24

<210> SEQ ID NO 3
<211> LENGTH: 24
<212> TYPE: DNA
<213> ORGANISM: Homo sapiens

<400> SEQUENCE: 3
gcctcccaaa gtgctgggat taca                                         24

<210> SEQ ID NO 4
<211> LENGTH: 29
<212> TYPE: DNA
<213> ORGANISM: Artificial
<220> FEATURE:
<223> OTHER INFORMATION: Mu(G-tail) probe

<400> SEQUENCE: 4
tagggttagg gttagggtta gggttaggg                                    29
```

<210> SEQ ID NO 5
<211> LENGTH: 29
<212> TYPE: DNA
<213> ORGANISM: Artificial
<220> FEATURE:
<223> OTHER INFORMATION: Mut1 probe

<400> SEQUENCE: 5
ccctaaccat aaccctaacc ctaaccta                                29

<210> SEQ ID NO 6
<211> LENGTH: 29
<212> TYPE: DNA
<213> ORGANISM: Artificial
<220> FEATURE:
<223> OTHER INFORMATION: Mut2 probe

<400> SEQUENCE: 6
ccctaaccat aaccctaacc ctaaccta                                29

<210> SEQ ID NO 7
<211> LENGTH: 29
<212> TYPE: DNA
<213> ORGANISM: Artificial
<220> FEATURE:
<223> OTHER INFORMATION: Mut3 probe

<400> SEQUENCE: 7
ccctaaccat aaccctaacc ctaaccta                                29

<210> SEQ ID NO 8
<211> LENGTH: 30
<212> TYPE: DNA
<213> ORGANISM: Artificial
<220> FEATURE:
<223> OTHER INFORMATION: C-strand of control for sensitivity test

<400> SEQUENCE: 8
ctaaccctaa ccctatagtg agtcgtatta                              30

<210> SEQ ID NO 9
<211> LENGTH: 40
<212> TYPE: DNA
<213> ORGANISM: Artificial
<220> FEATURE:
<223> OTHER INFORMATION: Gt10 control for sensitivity test

<400> SEQUENCE: 9
taatacgact cactataggg ttagggttag ggttagggtt                   40

<210> SEQ ID NO 10
<211> LENGTH: 50
<212> TYPE: DNA
<213> ORGANISM: Artificial
<220> FEATURE:
<223> OTHER INFORMATION: Gt20 control for sensitivity test

<400> SEQUENCE: 10
taatacgact cactataggg ttagggttag ggttagggtt agggttaggg        50

<210> SEQ ID NO 11
<211> LENGTH: 56
<212> TYPE: DNA
<213> ORGANISM: Artificial
<220> FEATURE:

<223> OTHER INFORMATION: Gt26 control for sensitivity test

<400> SEQUENCE: 11
taatacgact cactataggg ttagggttag ggttagggtt agggttaggg ttaggg          56

<210> SEQ ID NO 12
<211> LENGTH: 74
<212> TYPE: DNA
<213> ORGANISM: Artificial
<220> FEATURE:
<223> OTHER INFORMATION: Gt43 control for sensitivity test

<400> SEQUENCE: 12
taatacgact cactataggg ttagggttag ggttagggtt agggttaggg ttagggttag       60
ggttagggtt aggg                                                        74

<210> SEQ ID NO 13
<211> LENGTH: 92
<212> TYPE: DNA
<213> ORGANISM: Artificial
<220> FEATURE:
<223> OTHER INFORMATION: Gt62 control for sensitivity test

<400> SEQUENCE: 13
taatacgact cactataggg ttagggttag ggttagggtt agggttaggg ttagggttag       60
ggttagggtt agggttaggg ttagggttag gg                                    92

<210> SEQ ID NO 14
<211> LENGTH: 27
<212> TYPE: DNA
<213> ORGANISM: Artificial
<220> FEATURE:
<223> OTHER INFORMATION: A1a probe

<400> SEQUENCE: 14
gaacagtgta tatcaatgag ttacaat                                          27

<210> SEQ ID NO 15
<211> LENGTH: 27
<212> TYPE: DNA
<213> ORGANISM: Artificial
<220> FEATURE:
<223> OTHER INFORMATION: A1b probe

<400> SEQUENCE: 15
gaacagtgta tatcaatgag ttacaat                                          27

<210> SEQ ID NO 16
<211> LENGTH: 25
<212> TYPE: DNA
<213> ORGANISM: Artificial
<220> FEATURE:
<223> OTHER INFORMATION: A2a probe

<400> SEQUENCE: 16
cgttggaaac gggatttgta gaaca                                            25

<210> SEQ ID NO 17
<211> LENGTH: 25
<212> TYPE: DNA
<213> ORGANISM: Artificial
<220> FEATURE:
<223> OTHER INFORMATION: A2b probe

<400> SEQUENCE: 17

```
cgttggaaac gggatttgta gaaca                                              25

<210> SEQ ID NO 18
<211> LENGTH: 22
<212> TYPE: DNA
<213> ORGANISM: Artificial
<220> FEATURE:
<223> OTHER INFORMATION: B2_1b probe

<400> SEQUENCE: 18
gtctgaagac agctacagtg ta                                                 22

<210> SEQ ID NO 19
<211> LENGTH: 21
<212> TYPE: DNA
<213> ORGANISM: Artificial
<220> FEATURE:
<223> OTHER INFORMATION: B2_2a probe

<400> SEQUENCE: 19
ccgactgctc ttctgaaggt c                                                  21

<210> SEQ ID NO 20
<211> LENGTH: 21
<212> TYPE: DNA
<213> ORGANISM: Artificial
<220> FEATURE:
<223> OTHER INFORMATION: B2_2b probe

<400> SEQUENCE: 20
ccgactgctc ttctgaaggt c                                                  21
```